US008601860B2

(12) United States Patent
Wakamatsu et al.

(10) Patent No.: US 8,601,860 B2
(45) Date of Patent: Dec. 10, 2013

(54) SENSING DEVICE AND SENSING METHOD

(75) Inventors: Shunichi Wakamatsu, Sayama (JP); Tomoya Yorita, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 721 days.

(21) Appl. No.: 12/802,467

(22) Filed: Jun. 8, 2010

(65) Prior Publication Data
US 2010/0313636 A1    Dec. 16, 2010

(30) Foreign Application Priority Data

Jun. 16, 2009   (JP) ................................ 2009-143588

(51) Int. Cl.
*G01N 29/02*   (2006.01)
(52) U.S. Cl.
USPC ................... 73/64.53; 73/61.49; 73/61.79
(58) Field of Classification Search
USPC .................................. 73/61.79, 64.53, 61.49
See application file for complete search history.

(56) References Cited

U.S. PATENT DOCUMENTS

| | | | | |
|---|---|---|---|---|
| 7,036,375 | B2 * | 5/2006 | Nozaki | .......................... 73/579 |
| 8,176,772 | B2 | 5/2012 | Wakamatsu | |
| 2002/0103352 | A1 * | 8/2002 | Sudor | ......................... 536/23.1 |
| 2009/0291509 | A1 * | 11/2009 | Wakamatsu | .................. 436/543 |
| 2010/0021346 | A1 | 1/2010 | Wakamatsu et al. | |
| 2010/0236331 | A1 | 9/2010 | Wakamatsu | |

FOREIGN PATENT DOCUMENTS

| | | |
|---|---|---|
| JP | 11-183479 | 7/1999 |
| JP | 2000-338022 | * 12/2000 |
| JP | 2004-245613 | 9/2004 |
| JP | 2005-331445 | * 12/2005 |
| JP | 2006-258787 | 9/2006 |
| JP | 2007-010538 | 1/2007 |
| JP | 2007-040717 | 2/2007 |
| JP | 2007-108170 | 4/2007 |
| JP | 2008-058086 | 3/2008 |

(Continued)

OTHER PUBLICATIONS

Zhang, B. et al., "A Novel Piezoelectric Quartz Micro-Array Immunosensor Based on Self-Assembled Monolayer for Determination of Human Chorionic Gonadotropin", Biosensors and Bioelectronics, vol. 19, Issue 7, Feb. 15, 2004, pp. 711-720.*

*Primary Examiner* — Daniel S Larkin
(74) *Attorney, Agent, or Firm* — Jordan and Hamburg LLP

(57) ABSTRACT

To provide a sensing device and a sensing method that, by a simple method of liquid supply to first and second excitation electrodes, makes it possible to make a first oscillation area adsorb an adsorption substance that adsorbs a substance to be sensed in a sample solution and a blocking substance that prevents the adsorption of a substance and to make the electrode in a second oscillation area adsorb the blocking substance. By the supply of a solution containing the adsorption substance to a first liquid storage space 53A surrounding a first excitation electrode 42A, a front surface of the excitation electrode 42A is made to adsorb the adsorption substance, and next, by the supply of a solution containing the blocking substance to the first liquid storage space 53A, an area, of the excitation electrode 42A, on which the adsorption substance is not adsorbed, is made to adsorb the blocking substance. Further, by the supply of the solution containing the blocking substance to a second liquid storage space 53B separated from the first liquid storage space and surrounding a second excitation electrode 42B, a front surface of the second excitation electrode 42B is made to adsorb the blocking substance.

6 Claims, 15 Drawing Sheets

(56) References Cited

FOREIGN PATENT DOCUMENTS

| JP | 2008-102118 | * | 5/2008 |
| JP | 2008-107167 | | 5/2008 |
| JP | 2008-248703 | | 10/2008 |
| JP | 2008-292270 | | 12/2008 |
| WO | WO-2005/031316 | | 4/2005 |
| WO | WO 2008/111624 | * | 9/2008 |

* cited by examiner (a)

(b)

(c)

(a)

(b)

(c)

SENSING DEVICE AND SENSING METHOD

BACKGROUND OF THE INVENTION

1. Field of the Invention

The present invention relates to a sensing device and a sensing method for recognizing a substance to be sensed contained in a sample solution and determining its quantity based on a frequency of a piezoelectric resonator such as a quartz-crystal resonator.

2. Description of the Related Art

As a device detecting a trace amount of a substance contained in a sample solution, there has been known a quartz-crystal sensor utilizing a quartz-crystal resonator, and a detection principle of such a quartz-crystal sensor is that an oscillation frequency (resonance frequency) of the quartz-crystal resonator changes when it adsorbs a trace amount of a substance. For example, in such a quartz-crystal sensor, an adsorption layer made of a biological substance film or the like that recognizes a specific substance to be sensed to react therewith is formed on a front surface of a metal electrode (excitation electrode) provided on a quartz-crystal piece. When the adsorption layer is brought into contact with the sample solution, the adsorption layer reacts with the substance to be sensed contained in the sample solution to adsorb the substance to be sensed, resulting in a mass change in the adsorption layer. Since a natural frequency of the quartz-crystal resonator changes according to the mass change of the adsorption layer, the concentration of the substance to be sensed is measured by using this action. As the biological substance film, a film of an antibody reacting with a specific antigen (substance to be sensed) is used, for instance, and this film of the antibody adsorbs the antigen.

A patent document 1 proposes a flow-cell sensor using a quartz-crystal resonator. In this sensor, the quartz-crystal resonator in which an electrode is formed is provided via silicon rubber between a support substrate and a cover having a solution inflow channel and a solution discharge channel. In the silicon rubber, a hole portion for storing a solution is formed, and a flow cell is formed by the cover, the quartz-crystal resonator, and the silicon rubber, and the solution supplied from the inflow channel is discharged from an outflow side after flowing onto the electrode of the quartz-crystal resonator to come into contact with the electrode. Being capable of continuous supply of a liquid, such a flow-cell sensor has advantages that a frequency characteristic can be easily stabilized, the liquid can be smoothly replaced, and only a small amount of a sample solution is necessary. Further, for forming an adsorption layer in this quartz-crystal sensor, a solution containing an adsorption substance is injected into the quartz-crystal sensor, whereby the adsorption substance is adsorbed by a front surface of the metal electrode.

Incidentally, the frequency change is caused also by the adhesion of a substance other than the substance to be sensed in the sample solution, for example, the adhesion of an unintended antigen or the like, to the quartz-crystal resonator or by the viscosity of the sample solution. Therefore, to enhance detection accuracy of a trace amount of the substance, it is necessary to take a measure for eliminating a frequency change caused by a disturbance such as the adhesion of the unintended substance. Here, as a method of reducing the influence of a disturbance such as a temperature change in the quartz-crystal sensor, a structure of a patent document 2 has been proposed. In this method, there is proposed a structure in which a first quartz-crystal resonator and a second quartz-crystal resonator are formed by using a common quartz-crystal piece, an adsorption substance is made to be adsorbed by an excitation electrode of one of the quartz-crystal resonators to form an adsorption layer, and the other quartz-crystal resonator is used as a reference, whereby a frequency change accompanying the temperature change is cancelled.

For higher accuracy detection, it is necessary to make an area in the excitation electrode of one of the quartz-crystal resonators, where no adsorption substance is adsorbed, and a front surface of an excitation electrode of the reference quartz-crystal resonator adsorb a blocking substance. This blocking substance is made of a component that does not adsorb a substance such as, for example, a protein, and the reason why the electrode is made to adsorb the blocking substance is to prevent the substance to be sensed from being adsorbed by the area in the front surface of the electrode, where no adsorption layer is adsorbed, thereby forming an environment where the substance to be sensed is adsorbed only by the adsorption substance and to prevent the adhesion of components other than the substance to be sensed, thereby ensuring high accuracy regarding a correspondence relation between an amount of the substance to be sensed captured by the adsorption substance and the frequency.

In the fabrication of the sensor including the two quartz-crystal resonators, it is necessary to make the excitation electrode of one of the quartz-crystal resonators adsorb the adsorption substance and the blocking substance and make the excitation electrode of the other quartz-crystal resonator adsorb only the blocking substance. However, when the flow-cell method is adopted in the structure where the first quartz-crystal resonator and the second quartz-crystal resonator are formed on the common quartz-crystal piece, the use of the aforesaid method of injecting the solution containing the adsorption substance into the quartz-crystal sensor and then injecting the solution containing the blocking substance into the quartz-crystal sensor results in the adsorption of the adsorption substance and the blocking substance by the excitation electrodes of the both quartz-crystal resonators.

To solve this, the following method is in practice. After the excitation electrode of the reference quartz-crystal resonator is made to adsorb the blocking substance in advance, the reference quartz-crystal resonator is mounted in the quartz-crystal sensor, then the solution containing the adsorption substance and the solution containing the blocking substance are sequentially injected into the quartz-crystal sensor, and the excitation electrode of the one quartz-crystal resonator is made to adsorb the adsorption substance and the blocking substance. At this time, the solution containing the adsorption substance and the solution containing the blocking substance are sequentially supplied also to the reference quartz-crystal resonator, but since the blocking substance is formed in advance on the excitation electrode of this quartz-crystal resonator, the blocking substance prevents the adsorption of the adsorption substance. This method, however, has problems that an operator has to take an increased trouble due to the need for the pre-process of making the reference quartz-crystal resonator adsorb the blocking substance in advance and the measurement time including the pre-process increases.

[Patent document 1] Japanese Patent Application Laid-open No. Hei 11-183479
[Patent document 2] Japanese Patent Application Laid-open No. 2007-108170

SUMMARY OF THE INVENTION

The present invention was made in consideration of the above circumstances, and has an object to provide a sensing device and a sensing method that make it possible, by a simple method, to make an electrode in contact with a sample solution in a first oscillation area adsorb an adsorption substance that adsorbs a substance to be sensed in the sample solution and a blocking substance that prevents the adsorption of a substance, and make an electrode in contact with the sample solution in a second oscillation area adsorb the blocking substance that prevents the adsorption of a substance.

A sensing device of the present invention is a sensing device in which a piezoelectric resonator having a first oscillation area and a second oscillation area formed on a common piezoelectric piece and oscillating independently of each other is mounted and which senses a substance to be sensed in a sample solution based on variations in oscillation frequencies of both oscillation areas when the sample solution is brought into contact with one surface side of the piezoelectric resonator, the sensing device including:

a first space forming member forming a first liquid storage space for liquid supply to one surface side of the first oscillation area;

a second space forming member forming a second liquid storage space for liquid supply to one surface side of the second oscillation area, the second liquid storage space being separated from the first liquid storage space;

a supply channel supplying a solution containing an adsorption substance that adsorbs the substance to be sensed in the sample solution, selectively to the first liquid storage space to make an electrode in the first oscillation area adsorb the adsorption substance;

a supply channel supplying a solution containing a blocking substance that prevents the adsorption of a substance to the first liquid storage space and the second liquid storage space in order to make the electrode in the first oscillation area and an electrode in the second oscillation area adsorb the blocking substance;

a supply channel supplying the sample solution to the first liquid storage space and the second liquid storage space; and a liquid discharge channel for liquid discharge from the first liquid storage space and the second liquid storage space.

The sensing device of the present invention may further include: a first supply channel and a second supply channel connected to the first liquid storage space and the second liquid storage space respectively; a common channel connected to upstream sides of the first supply channel and the second supply channel and supplying the sample solution, the solution containing the adsorption substance, and the solution containing the blocking substance at different timings; and a channel switcher switchably connecting the common channel to one of the first supply channel and the second supply channel.

The sensing device of the present invention may further include: a reference liquid supply source provided on an upstream side of the common channel to supply a reference liquid not containing the substance to be sensed; and a controller controlling the channel switcher to cause the supply of the solution containing the adsorption substance, the solution containing the blocking substance, the reference liquid, and the sample solution in the order cited to the first supply channel and the supply of the solution containing the blocking substance, the reference liquid, and the sample solution in the order cited to the second supply channel.

Here, the adsorption substance can be an antibody and the substance to be sensed in the sample solution can be an antigen. Further, in the first space forming member and the second space forming member, at least portions in contact with the piezoelectric resonator are each preferably made of an elastic member.

A sensing method of the present invention is a sensing method in which a piezoelectric resonator having a first oscillation area and a second oscillation area formed on a common piezoelectric piece and oscillating independently of each other is mounted and a substance to be sensed in a sample solution is sensed based on variations in oscillation frequencies of both oscillation areas when the sample solution is brought into contact with one surface side of the piezoelectric resonator, the sensing method using a first space forming member forming a first liquid storage space for liquid supply to one surface side of the first oscillation area and a second space forming member forming a second liquid storage space for liquid supply to one surface side of the second oscillation area, the second liquid storage space being separated from the first liquid storage space, and the sensing method including:

supplying a solution containing an adsorption substance that adsorbs the substance to be sensed in the sample solution to the first liquid storage space to make an electrode in the first oscillation area adsorb the adsorption substance;

next supplying a solution containing a blocking substance that prevents the adsorption of a substance, to the first liquid storage space to make the electrode in the first oscillation area adsorb the blocking substance;

supplying the solution containing the blocking substance to the second liquid storage space to make an electrode in the second oscillation area adsorb the blocking substance;

supplying a reference liquid not containing the substance to be sensed and the sample solution in the order cited to the first liquid storage space to measure the oscillation frequency of the first oscillation area; and supplying the reference liquid not containing the substance to be sensed and the sample solution in the order cited to the second liquid storage space to measure the oscillation frequency of the second oscillation area.

In the present invention, in the sensing device in which the piezoelectric resonator having the first oscillation area and the second oscillation area formed on the common piezoelectric piece and oscillating independently of each other is mounted, since the first liquid storage space for liquid supply to one surface side of the first oscillation area and the second liquid storage space for liquid supply to one surface side of the second oscillation area are separately formed, the liquid supply separately to the first liquid storage space and the second liquid storage space is possible. This makes it possible to supply the first liquid storage space with the solution containing the adsorption substance that adsorbs the substance to be sensed in the sample solution and the solution containing the blocking substance that prevents the adsorption of a substance and supply the second liquid storage space with the solution containing the blocking substance. By such a simple method of separately supplying the liquids to the liquid storage spaces, it is possible to make the electrode in the first oscillation area adsorb the adsorption substance and the blocking substance and make the electrode in the second oscillation area adsorb the blocking substance.

DETAILED DESCRIPTION OF THE PREFERRED EMBODIMENTS

Figure 1:
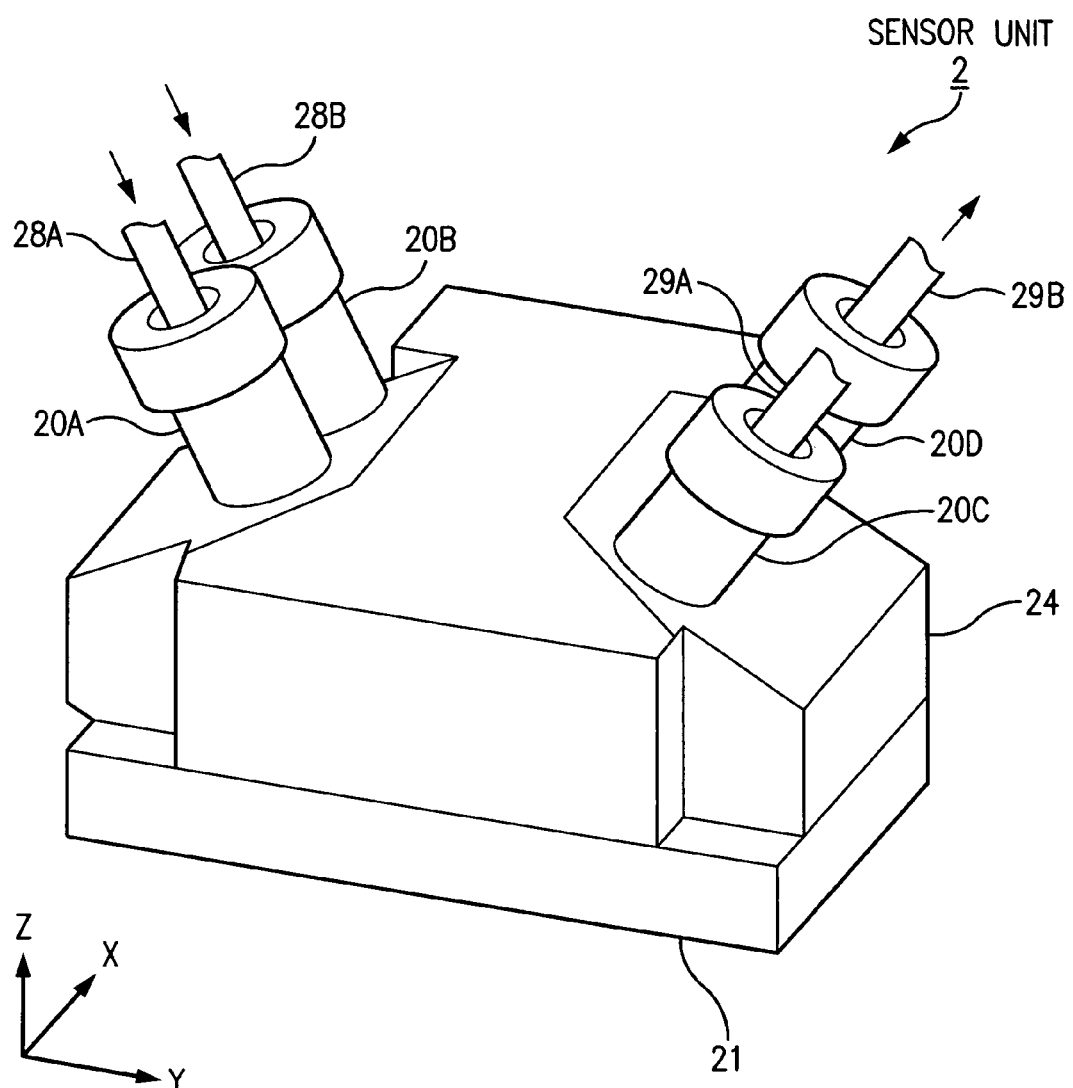
FIG. 1 is an external perspective view showing a sensor unit of a sensing device according to an embodiment of the present invention.
Figure 2:
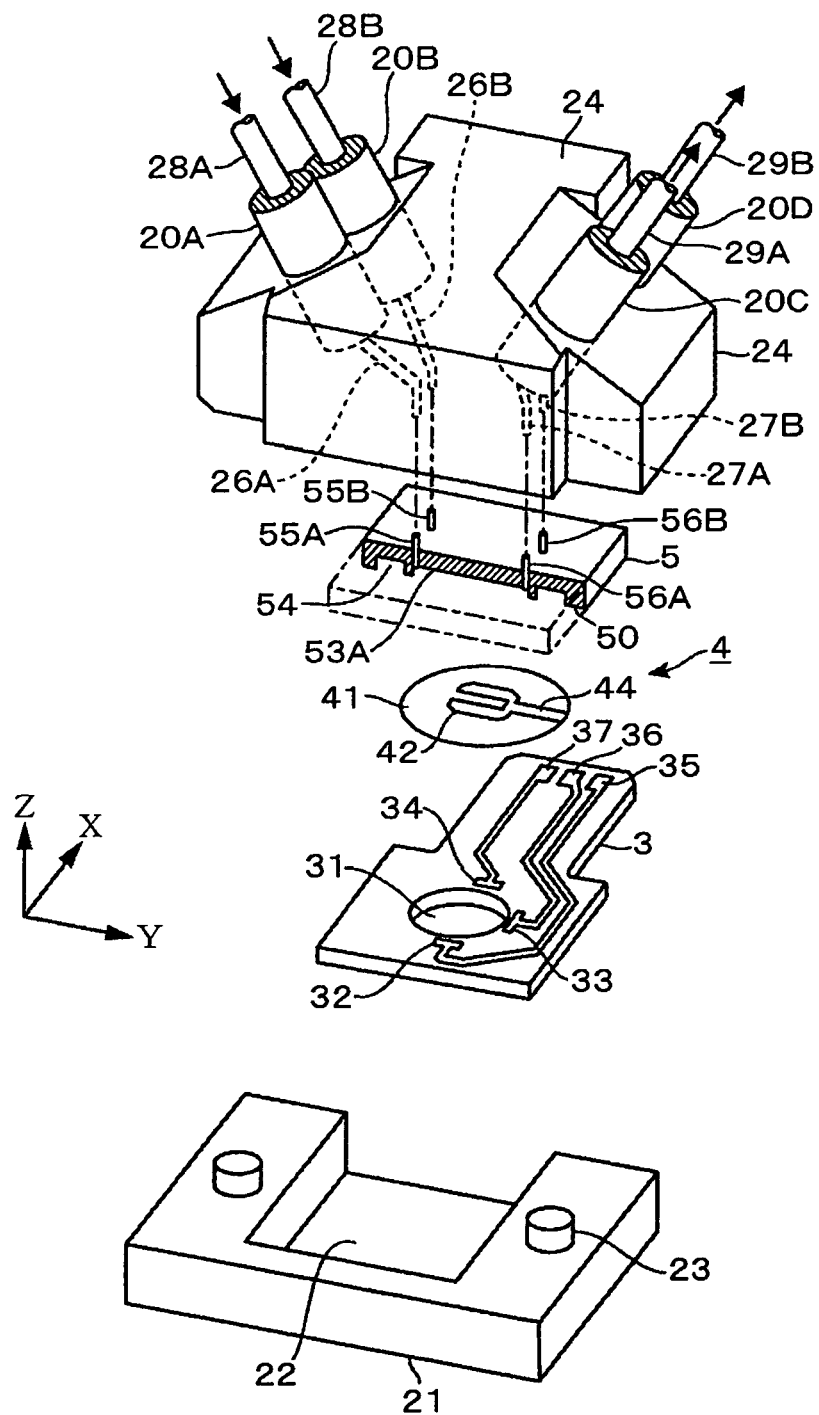
FIG. 2 is an exploded perspective view showing upper surface sides of components of the sensor unit.

Embodiments of a sensing device according to the present invention will be described by using the drawings. First, a sensor unit 2 including a quartz-crystal sensor being a piezoelectric sensor will be described. FIG. 1 is an external perspective view showing the sensor unit of the sensing device, and FIG. 2 is an exploded perspective view showing upper surface sides of components of the sensor unit. As shown in FIG. 2, the sensor unit 2 is composed of a support 21, a wiring board 3, a quartz-crystal resonator 4, a pressing member 5, and a liquid supply/discharge cover 24, and these components are stacked in this order from the bottom.

Figure 3A:
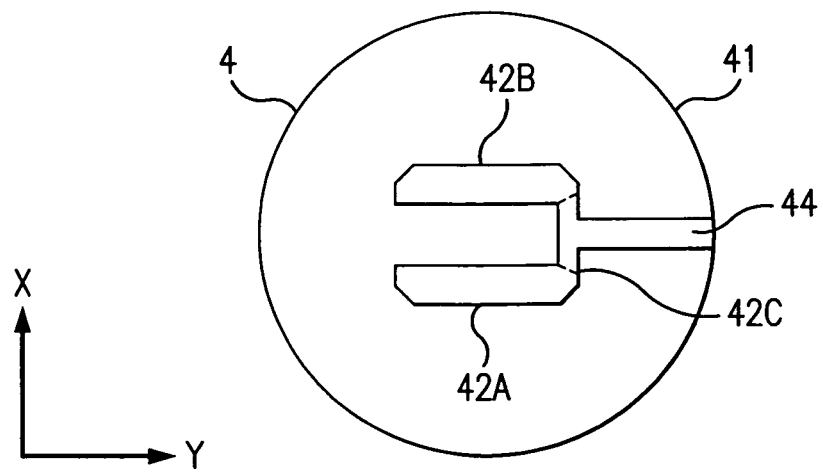
FIG. 3(a) and FIG. 3(b) are a plane view and a bottom view, respectively, showing excitation electrodes provided on a quartz-crystal piece.
Figure 3B:
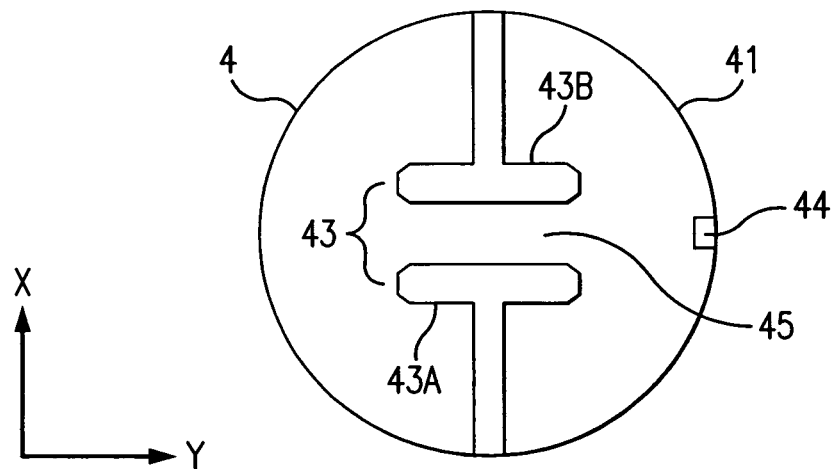

The quartz-crystal sensor has the quartz-crystal resonator 4 being a piezoelectric resonator provided on the wiring board 3, and the quartz-crystal resonator 4 will be described by using FIG. 2 to FIG. 4. The quartz-crystal resonator 4, as shown in its plane view and its bottom view in FIG. 3(a) and FIG. 3(b) respectively, is structured such that excitation electrodes 42, 43 for exciting a quartz-crystal piece 41 in a circular plate shape being a piezoelectric piece are provided on center portions of a front surface and a rear surface of the quartz-crystal piece 41. The, excitation electrode 42 provided on the front surface side includes two excitation electrodes 42A, 42B (a first excitation electrode 42A, a second excitation electrode 42B) in a substantially strip shape extending in a longitudinal direction (Y direction in FIG. 1 to FIG. 3(b)), and these excitation electrodes 42A, 42B are provided in parallel with each other, being apart from each other in a width direction (X direction in FIG. 1 to FIG. 3(b)). Further, an electrode film 42C is connected to one end of each of the excitation electrodes 42A, 42B in a longitudinal direction of such electrodes 42A, 42B. A lead electrode 44 is connected to the electrode film 42C, and the lead electrode 44 is formed so as to be drawn out toward a peripheral edge on one-end side of the quartz-crystal piece 41 and bent along an end surface of the quartz-crystal piece 41 to be led to the rear surface side. The excitation electrodes 42A, 42B, the electrode film 42C and the lead electrode 44 are integrally formed.

Figure 4:
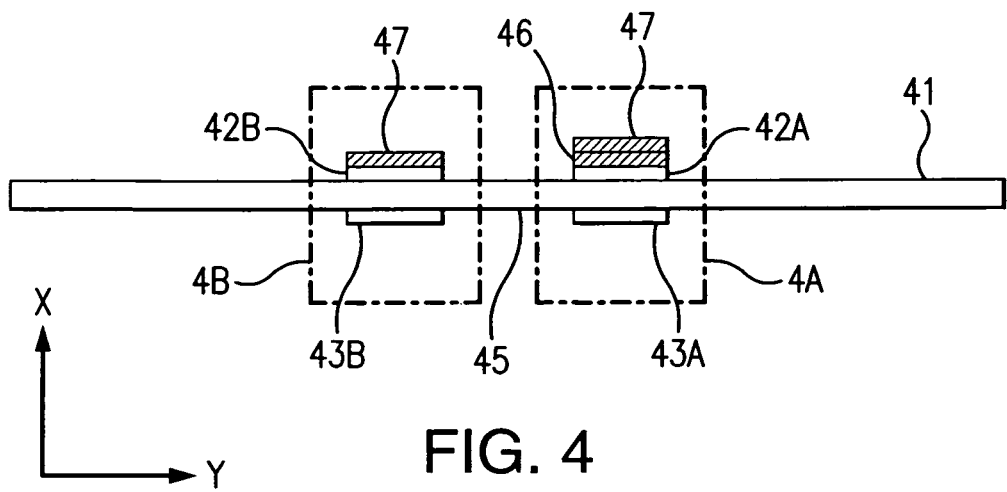
FIG. 4 is a vertical sectional view showing a first oscillation area and a second oscillation area provided on the quartz-crystal piece.

The excitation electrode 43 provided on the rear surface side is formed in the same layout as the two excitation electrodes 42A, 42B so as to face the two excitation electrodes 42A, 42B on the front surface side across the quartz-crystal piece 41, as shown in FIG. 4. The excitation electrodes 42, 43, the electrode film 42C, and the lead electrode 44 each have, for example, a 0.2 gm equivalent thickness and are made of a foil film of metal such as gold (Au) or silver (Ag). Actually, a Cr film having a high joining property with quartz crystal is provided on surfaces of quartz crystal, and the Au film is stacked thereon. Later-described wirings each have such a stacked structure but are each shown as a single layer in the drawings for convenience sake.

In this example, on the common quartz-crystal piece 41, a first oscillation area 4A is constituted by an area where the excitation electrodes 42A, 43A are formed and a second oscillation area 4B is constituted by an area where the excitation electrodes 42B, 43B are formed. These first and second oscillation areas 4A, 4B are arranged, being a predetermined space 45 apart from each other and being parallel with each other, in the longitudinal direction thereof. The space 45 forms an elastic boundary area between the first and second oscillation areas 4A, 4B. In this structure, the first and second oscillation areas 4A, 4B oscillate independently of each other and the space 45 as the boundary area formed therebetween prevents the propagation of an elastic wave. In the structure where the first oscillation area 4A and the second oscillation area 4B are formed on the common quartz-crystal piece 41, they are equal in thickness and cutting angle of the quartz crystal and operate completely in the same manner. That is, with the same load capacitance, they oscillate with the same frequency and have the same frequency-temperature characteristic. Further, the excitation electrodes 42A, 42B, 43A, 43B are equal in size and in film thickness.

The excitation electrodes in one of the two oscillation areas 4A, 4B, for example, the excitation electrodes 42A, 43A in the first oscillation area 4A are used as reaction electrodes for detecting a substance to be sensed, and the excitation electrodes 42B, 43B in the other second oscillation area 4B, for example, are used as reference electrodes. For this purpose, an adsorption layer 46 containing an adsorption substance that adsorbs the substance to be sensed and a blocking layer 47 containing a blocking substance that prevents the adsorption of a substance are formed on the excitation electrode 42A on the front surface side (side in contact with a sample solution) in the first oscillation area 4A, and only the blocking layer 47 is formed on the excitation electrode 42B on the front surface side in the second oscillation area 4B.

For example, when the sample solution is blood and the substance to be sensed is a specific antigen, for example, a C-reactive protein, the adsorption layer 46 is formed as a layer containing an antibody reacting with the antigen in the sample solution to capture the antigen, and as the antibody, one containing immunoglobulin such as IgG is used. Further, the blocking layer 47 is one containing a protein, for example. BSA (Bovine Serum Albumin). Actually, on a front surface of the excitation electrode 42A, as will be described later, an adsorption substance (antibody) 48 is adsorbed and a blocking substance 49 is adsorbed on an area other than the area on which the adsorption substance 48 is adsorbed (see FIG. 14).

Figure 5A:
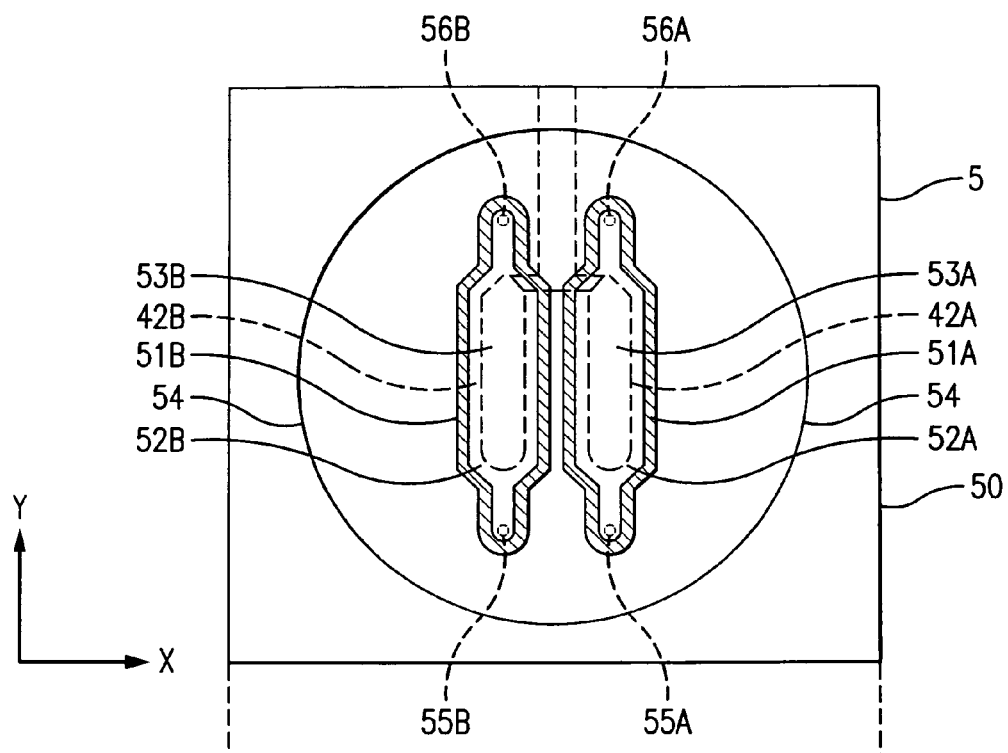
FIG. 5(a) and, FIG. 5(b) are a bottom view showing a pressing member and a vertical sectional view showing part of the sensor unit, respectively.
Figure 5B:
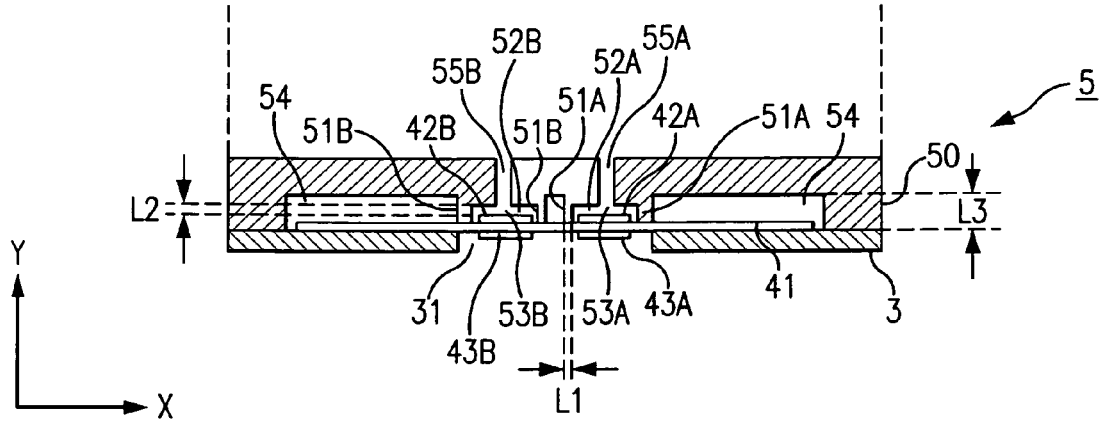
Figure 6:
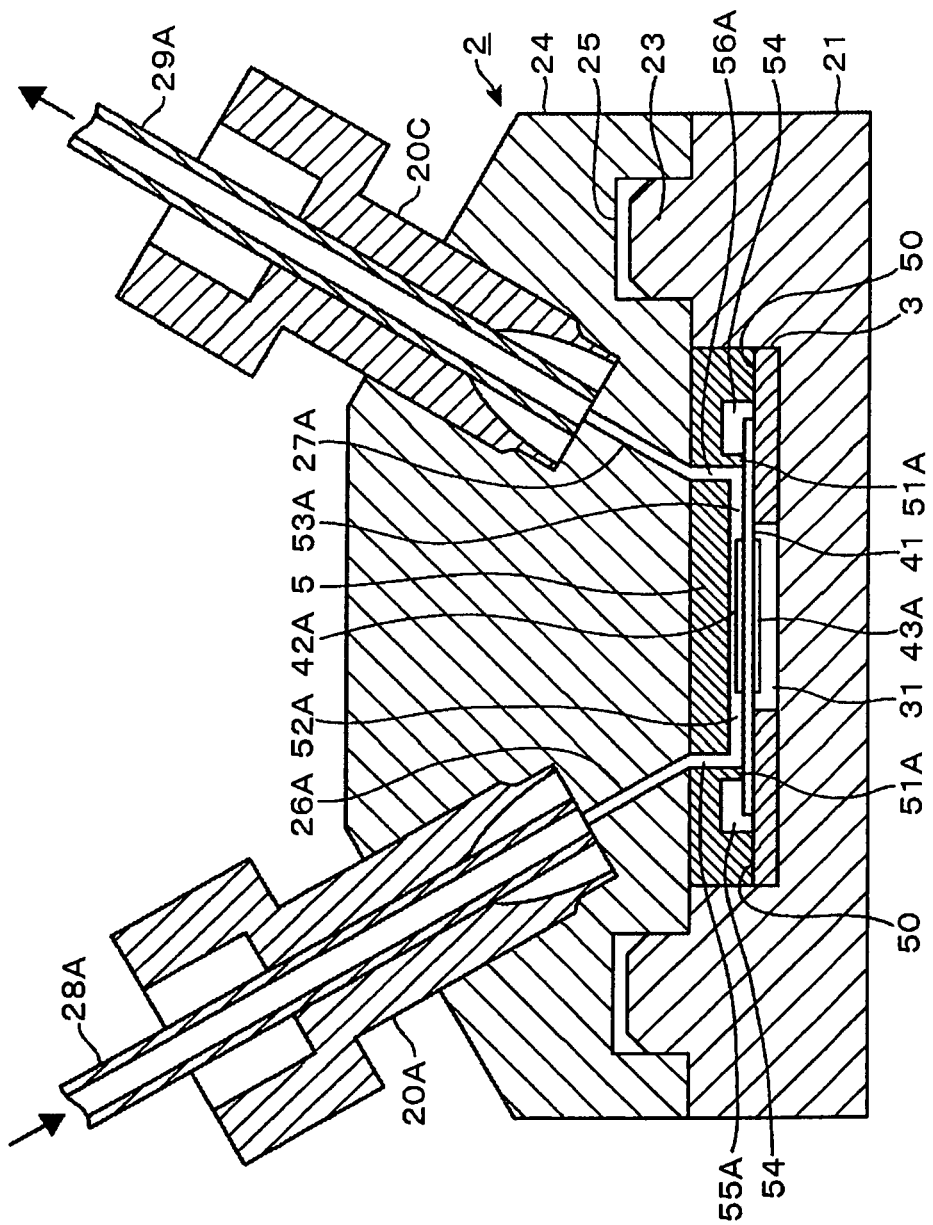
FIG. 6 is a view showing a vertical section of the sensor unit.

Next, the sensor unit 2 will be described with reference to FIG. 2. FIG. 5(a), FIG. 5(b), and FIG. 6. The wiring board 3 is constituted by, for example, a printed circuit board, and in the wiring board 3, formed is a through hole 31 serving as a concave portion forming an airtight space faced by the excitation electrodes 43A, 43B on the rear surface side of the quartz-crystal resonator 4, and the through hole 31 is formed to have a diameter large enough to house the excitation electrodes 43A, 43B. Further, on a front surface of the wiring board 3, an electrode 32, an electrode 33, and an electrode 34 (see FIG. 2) are provided around the through hole 31 at spaced intervals. The electrodes 32, 33, 34 are formed so as to be electrically connected to the excitation electrode 43A on the rear surface side, the lead electrode 44 led to the rear surface side from the front surface side, and the excitation electrode 43B on the rear surface side respectively when the quartz-crystal resonator 4, is disposed on the wiring board 3. On a back end side of the wiring board 3, there are provided connection terminal 35, 36, 37, which are electrically connected to the electrodes 32. 33, 34 (see FIG. 2) via conductive paths respectively. Among them, the connection terminal 36 is connected to the ground.

The pressing member 5 is formed in a shape corresponding to the wiring board 3 by using an elastic member, for example, silicon rubber, and as shown in FIG. 5(a), FIG. 5(b), and FIG. 6, a lower surface of a rim area 50 of the pressing member 5 is in contact with an area, of the wiring board 3, outside the quartz-crystal resonator 4. Incidentally, in the pressing member 5, at least the portion in contact with the quartz-crystal resonator 4 only needs to be made of the elastic member. The pressing member 5 plays a role of not only pressing the quartz-crystal resonator 4 against the wiring board 3 but also demarcating and forming separate liquid storage spaces on the excitation electrode 42A in the first oscillation area 4A and on the excitation electrode 42B in the second oscillation area 4B. For this purpose, a bottom surface of the pressing member 5 includes a first annular projection 51A and a second annular projection 51B individually surrounding peripheries of the two excitation electrodes 42A, 42B respectively on the front surface side of the quartz-crystal resonator 4.

FIG. 5(a) and FIG. 5(b) are a bottom view and a vertical sectional view of the pressing member 5, respectively. As shown, bottom surfaces of the annular projections 51A, 51B are formed in a shape so as to surround the whole outer peripheries of the excitation electrodes 42A, 42B respectively via small gaps when the pressing member 5 is pressed against the front surface of the quartz-crystal resonator 4. In this example, the excitation electrode 42 on the front surface side is in a C shape in a plane view, and since the liquid storage spaces only need to be formed on the front surface sides of the excitation electrodes 42A, 42B in the first and second oscillation areas 4A, 4B, the first annular projection 51A is formed so as to surround the first excitation electrode 42A and the second annular projection 51B is formed so as to surround the second excitation electrode 42B. A width L1 of the bottom surfaces of the annular projections 51A, 51B, that is, the width L1 of contact portions between the annular projections 51A, 51B and the quartz-crystal piece 41 is set to about 0.45 mm, for instance.

Further, in inner areas of the annular projections 51A, 51B in the pressing member 5, that is, in areas facing upper sides of the excitation electrodes 42A, 42B, concave portions 52A, 52B which are indented when viewed from a bottom surface side of the pressing member 5 are formed so as to form ceiling surfaces facing the excitation electrodes 42A, 42B via predetermined spaces. In this manner, when the pressing member 5 is pressed against the front surface of the quartz-crystal resonator 4, enclosed areas are formed on the front surfaces of the excitation electrodes 42A, 42B by the quartz-crystal resonator 4, the annular projections 51A, 51B, and the concave portions 52A, 52B, and these areas form liquid storage spaces 53A, 53B that are areas where the sample solution and so on are brought into contact with the excitation electrodes 42A, 42B on the front surface of the quartz-crystal resonator 4 and are areas for storing the sample solution and so on.

In this example, a first space forming member forming the first liquid storage space 53A for liquid supply onto the first excitation electrode 42A is composed of the first annular projection 51A and the concave portion 52A, and a second space forming member forming the second liquid storage space 53B for liquid supply onto the second excitation electrode 42B is composed of the second annular projection 51B and the concave portion 52B. The first space forming member and the second space forming member are formed by the single pressing member 5.

Further, in the pressing member 5, in the whole area outside the annular projections 51A, 51B, an outer concave portion 54 having a ceiling surface whose position is higher than ceiling surfaces of the inner concave portions 52A, 52B when seen from the quartz-crystal piece 41 is formed. The outer concave portion 54 is formed to have a circular shape in a plane view, and a rim thereof is located on an outer side of a rim of the quartz-crystal piece 41.

The heights of the ceiling surfaces of the liquid storage spaces 53A, 53B are set so that a distance L2 thereof from the front surfaces of the excitation electrodes 42A, 42B is, for example, about 0.1 mm to about 0.2 mm. and a height L3 of the ceiling surface of the outer area formed by the outer concave portion 54 is set so that a distance thereof from the front surface of the quartz-crystal piece 41 is, for example, about 0.7 mm. The reason why the ceiling surface in the outer area is thus higher than the ceiling surfaces of the liquid storage spaces 53A, 53B is to reserve an escape space of the thickness of a bonded portion of the quartz-crystal piece 41, but the height of the ceiling surface of the outer area may be equal to the heights of the ceiling surfaces of the liquid storage spaces 53A, 53B.

Further, on an upper surface of the pressing member 5, a first supply channel 55A and a second supply channel 55B for liquid supply to the first liquid storage space 53A and the second liquid storage space 53B respectively and a first discharge channel 56A and a second discharge channel 56B for liquid discharge from the first liquid storage space 53A and the second liquid storage space 53B respectively are formed. One-side ends of the supply channels 55A, 55B and the discharge channels 56A, 56B communicate with the liquid storage spaces 53A, 53B, respectively. In this example, as shown in FIG. 5(a) and FIG. 6, the supply channels 55A, 55B are connected to the one-side ends of the liquid storage spaces 53A, 53B and the discharge channels 56A, 56B are connected to the other ends thereof in terms of the longitudinal direction of the liquid storage spaces 53A, 53B (Y direction in FIG. 5(a). FIG. 5(b), and FIG. 6). Note that, in FIG. 2, the supply channels 55A, 55B and the discharge channels 56A, 56B are depicted in a tubular shape for convenience of illustration.

In the support 21, a concave portion 22 having a shape corresponding to the shape of the wiring board 3 is formed, and projections 23 are formed on parts of its upper surface. The wiring board 3 is housed in the concave portion 22. On a lower surface of the supply/discharge cover 24, concave portions 25 are formed, and the supply/discharge cover 24 is connected to the support 21 when the projections 23 provided on the support 21 are fit into the concave portions 25.

Further, as shown in FIG. 1 and FIG. 2, in the liquid supply/discharge cover 24, a first liquid supply channel 26A and a second liquid supply channel 26B communicating with the first supply channel 55A and the second supply channel 55B respectively are provided, and a first liquid discharge channel 27A and a second liquid discharge channel 27B communicating with the first discharge channel 56A and the second discharge channel 56B respectively are provided. A first liquid supply pipe 28A and a second liquid supply pipe 28B are connected to the first and second liquid supply channels 26A, 26B, respectively, and a first liquid discharge pipe 29A and a second liquid discharge pipe 29B are connected to the first and second liquid discharge channels 27A, 27B, respectively. In FIG. 1, reference numerals 20A and 20B denote supply ports, and reference numerals 20C and 20D denote discharge ports.

On the support 21, the bearing part 30, the wiring board 3, the quartz-crystal resonator 4, and the pressing member 5 are disposed, and the supply/discharge cover 24 is attached to the support 21, so that the rim area 50 of the pressing member 5 is pressed against the wiring board 3 and the first and second annular projections 51A, 51B press the quartz-crystal resonator 4 against the wiring board 3 to fix the position of the quartz-crystal resonator 4. At this time, by the annular projections 51A, 51B, the quartz-crystal resonator 4 is pressed against an area on an outer side of the through hole 31 formed in the wiring board 3, and consequently, the positions of the pressing member 5, the quartz-crystal resonator 4, and the wiring board 3 are fixed, and the first liquid storage space 53A and the second liquid storage space 53B are formed on the front surfaces of the first excitation electrode 42A and the second excitation electrode 42B, respectively.

Figure 9:
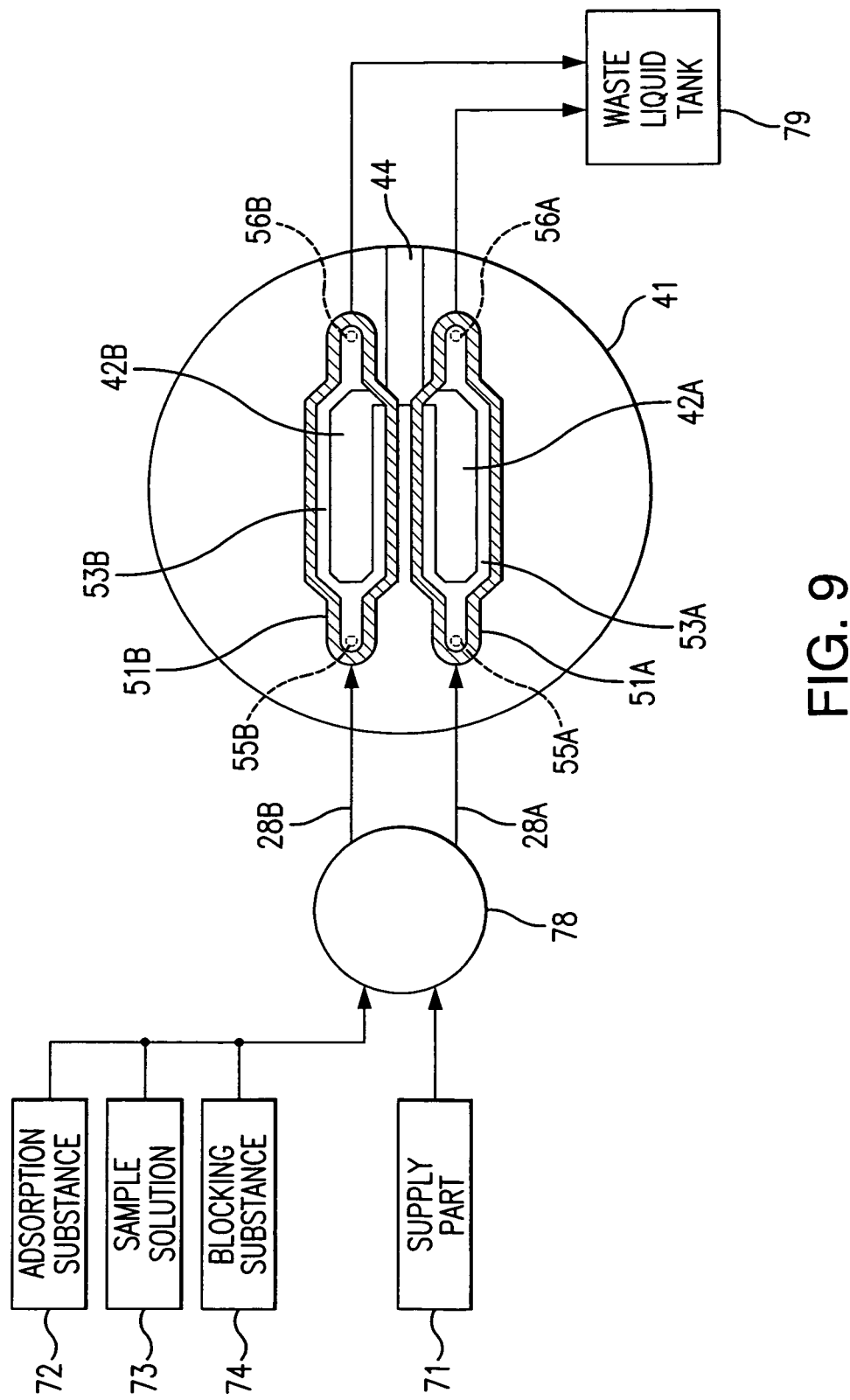
FIG. 9 is a plane view showing a first and a second liquid storage space formed in the first and second oscillation areas.

A liquid is supplied into the first liquid storage space 53A from the first liquid supply pipe 28A via the first liquid supply channel 26A and the first supply channel 55A, and the liquid flows in the liquid storage space 53A to be discharged from the liquid discharge pipe 29A via the first discharge channel 56A and the first liquid discharge channel 27A. Further, a liquid is supplied into the second liquid storage space 53B from the second liquid supply pipe 28B via the second liquid supply channel 26B and the second supply channel 55B, and the liquid flows in the liquid storage space 53B to be discharged from the second liquid discharge pipe 29B via the second discharge channel 56B and the second liquid discharge channel 27B. Thus, the first and second liquid storage spaces 53A, 53B serve as liquid channels. These liquid storage spaces 53A, 53B are formed larger than the excitation electrodes 42A, 42B, and a liquid is supplied from the positions outside the one-side ends of the excitation electrodes 42A, 42B via the first and second supply channels 55A, 55B and the liquid is discharged from the position outside the other ends of the excitation electrodes 42A, 42B via the first and second discharge channels 56A, 56B. Consequently, the liquid comes into contact with the whole excitation electrodes 42A, 42B in the first and second liquid storage spaces 53A, 53B (see FIG. 9).

Figure 7:
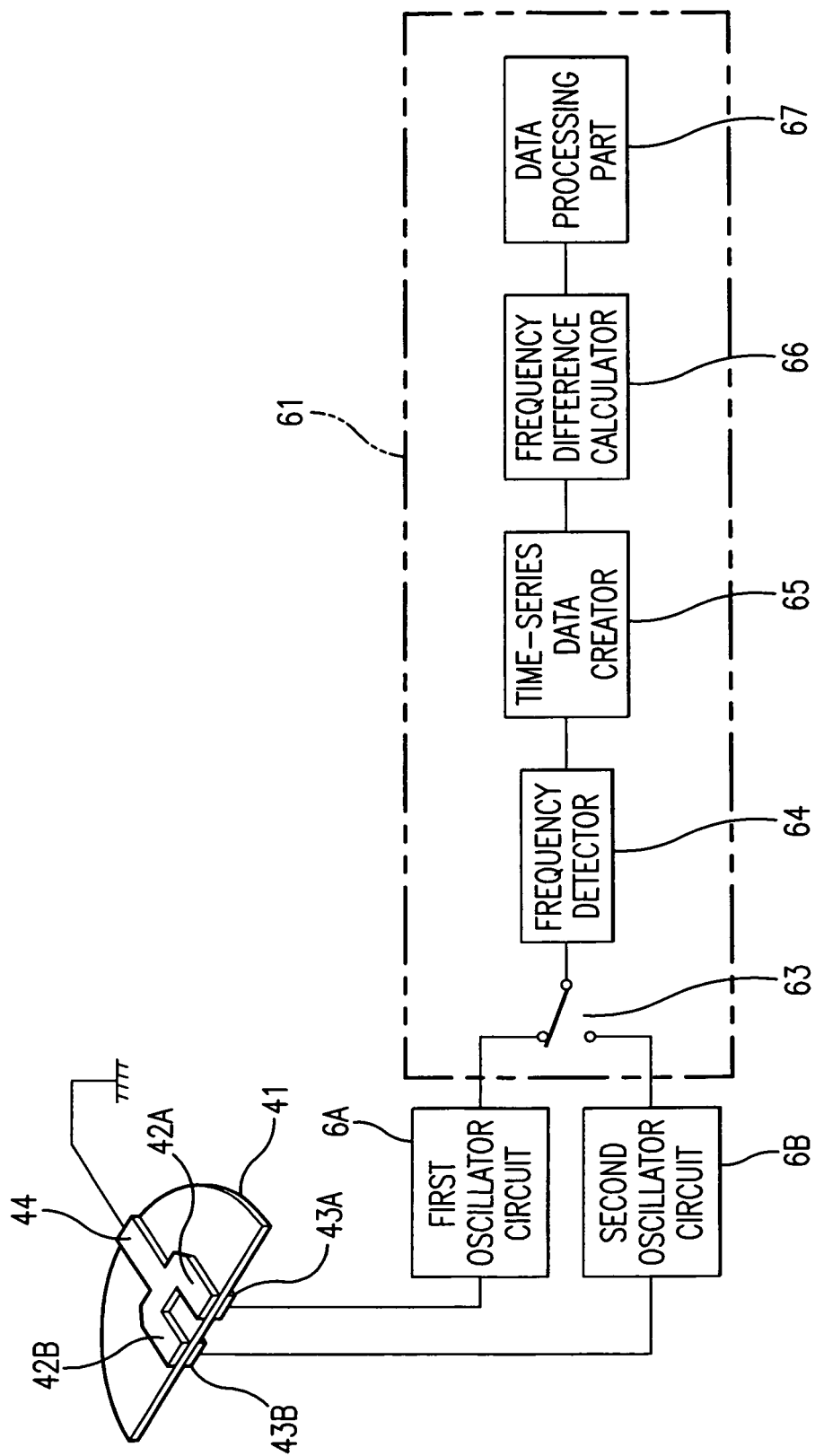
FIG. 7 is a block diagram showing an example of a measurement circuit part provided in the sensing device.

In the foregoing, the quartz-crystal resonator 4 and the wiring board 3 correspond to the piezoelectric sensor of the present invention. The rear surface side of the quartz-crystal resonator 4 is exposed to an airtight atmosphere surrounded by the wiring board 3 and the support 21. Therefore, this piezoelectric sensor constitutes a Languban-type quartz-crystal sensor. It should be noted that the atmosphere on the rear surface side of the quartz-crystal resonator 4 is not limited to the airtight atmosphere. As shown in FIG. 7, the first and second oscillation areas 4A, 4B are electrically connected to a first oscillator circuit 6A and a second oscillator circuit 6B of a Colpitts type, which are connected in series to the first and second oscillation areas 4A, 4B, respectively, via signal lines (not shown) connected to the connection terminals 35, 37 formed on the wiring board 3, so that oscillation frequencies are extracted from the first oscillation area 4A and the second oscillation area 4B. A measurement circuit part 61 and a display part 62 are electrically connected to the first oscillator circuit 6A and the second oscillator circuit 6B (see FIG. 8).

The measurement circuit part 61 includes a switch part 63, a frequency detector 64, a time-series data creator 65, a frequency difference calculator 66, and a data processing part 67. The switch part 63 plays a role of switchably fetching a frequency signal from one of the first and second oscillator circuits 6A, 6B. The frequency detector 64 digitally processes the frequency signals received from the first and second oscillator circuits 6A, 6B to measure the oscillation frequencies of the oscillation areas 4A, 4B. The frequency detector 64 may be one that detects the frequencies by a frequency counter, which is a publicly known circuit, but may be one that uses a method of A/D-converting the frequency signals, processing the resultants by a carrier move, generating rotation vectors rotating at the frequencies of the frequency signals, and finding the velocities of the rotation vectors, as described in, for example, Japanese Patent Application Laid-open No. 2006-258787. The use of the measuring part that performs such digital processing enables frequency detection with higher accuracy and therefore is more preferable.

Further, the time-series data creator 65 plays a role of obtaining time-series data regarding the oscillation frequencies received from the first and second oscillator circuits 6A, 6B to store the obtained time-series data in a memory. The frequency difference calculator 66 plays a role of obtaining difference data between a variation in the frequency of the first oscillator circuit 6A and a variation in the frequency of the second oscillator circuit 6B.

The data processing part 67 detects an amount of the substance to be sensed in the sample solution. When an amount of the substance to be sensed in the sample solution is expressed by a mass concentration, a pre-obtained calibration curve showing a variation in the difference data between the oscillation frequencies of the first oscillation area 4A and the second oscillation area 4B and the mass concentration of the substance to be sensed in the sample solution is stored, and based on the frequency variation calculated by the frequency difference calculator 66, the mass concentration of the substance to be sensed in the sample solution is found with reference to the calibration curve. For example, the detection result thus obtained is displayed on the display part 62.

Next, the whole structure of the sensing device according to an embodiment of the present invention will be described by using FIG. 8. The sensing device includes the sensor unit 2, the oscillator circuit 6 (6A, 6B), the measurement circuit part 61, the display part 62, a buffer solution reservoir part 71, an adsorption substance-containing solution supply part 72, a sample solution supply part 73, a blocking substance-containing solution supply part 74, a degassing part 75, a first valve 76, a second valve 77, a third valve 78, a waste liquid tank 79, and a control part 100.

The buffer solution reservoir part 71 stores a buffer solution, for example, a phosphoric acid buffer. The adsorption substance-containing solution supply part 72, the sample solution supply part 73, and the blocking substance-containing solution supply part 74 store a solution containing, for example, immunoglobulin which is an adsorption substance, a sample solution, for example, blood, and a solution containing, for example, BSA, which is a blocking substance, respectively, and are capable of supplying these liquids toward supply channels provided on downstream sides thereof at predetermined flow rates. As the adsorption substance-containing solution supply part 72, the sample solution supply part 73, and the blocking substance-containing solution supply part 74, pipettes or syringes are used, for instance. The liquid supply from these adsorption substance-containing solution supply part 72, sample solution supply part 73, and blocking substance-containing solution supply part 74 may be manual or may be automated based on a command from the control part 100.

Figure 10A:
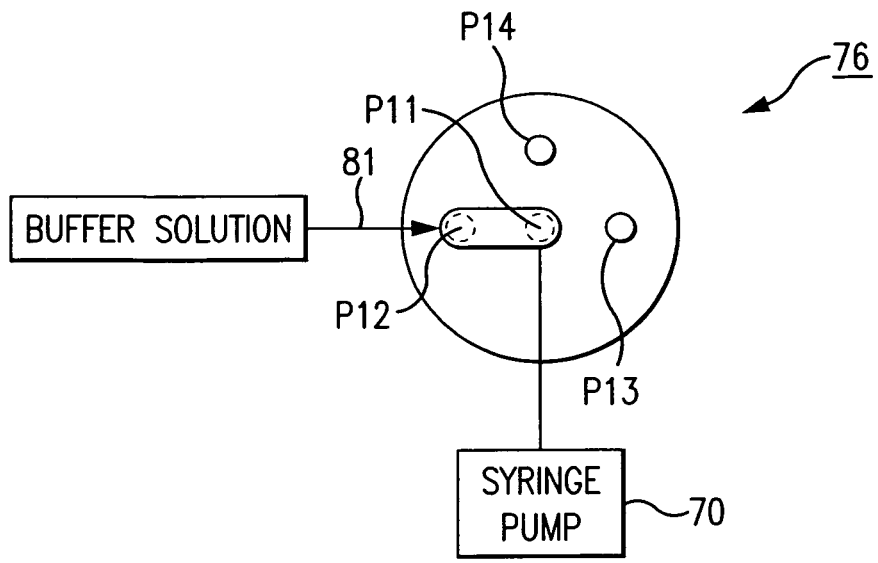
FIG. 10(a) and FIG. 10(b) are explanatory plane views showing switching control of a first valve provided in the sensing device.
Figure 10B:
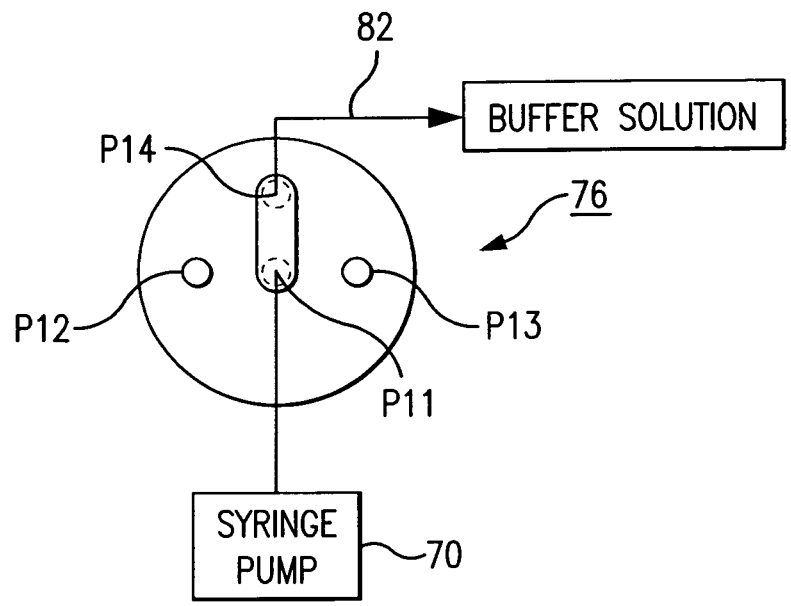

On a subsequent stage of the buffer solution reservoir part 71, a valved pump constituting the first valve 76 is provided via the degassing part 75. The reason why the degassing part 75 is provided is to remove bubbles from the buffer solution in advance because the presence of bubbles in the buffer solution might give an influence on hydraulic pressure and pressure and elasticity of a surface of the quartz crystal to make quartz-crystal oscillation unstable. The first valve 76 is composed of the combination of a buffer solution holding part, for example, a syringe pump 70 and a three-way valve. For example, the valve includes four ports P11 to P14 as shown in FIG. 8. FIG. 10(*a*), and FIG. 10(*b*), and among these ports, the port P12 is connected to the buffer solution reservoir part 71 by a supply channel 81 via the degassing part 75, and the port P14 is connected to the second valve 77 on a subsequent stage by a supply channel 82. The syringe pump 70 is structured to suck a predetermined amount of the buffer solution from the buffer solution reservoir part 71 to hold the sucked buffer solution. For example, by switching the valve so as to connect the port P11 and the port P12 as shown in FIG. 10(*a*), a predetermined amount of the buffer solution is sucked from the buffer solution reservoir part 71 into the pump 70, and as shown in FIG. 10(*b*), by switching the valve so as to connect the port P11 and the port P14, the buffer solution in the pump 70 is sent toward the supply channel 82.

Figure 8:
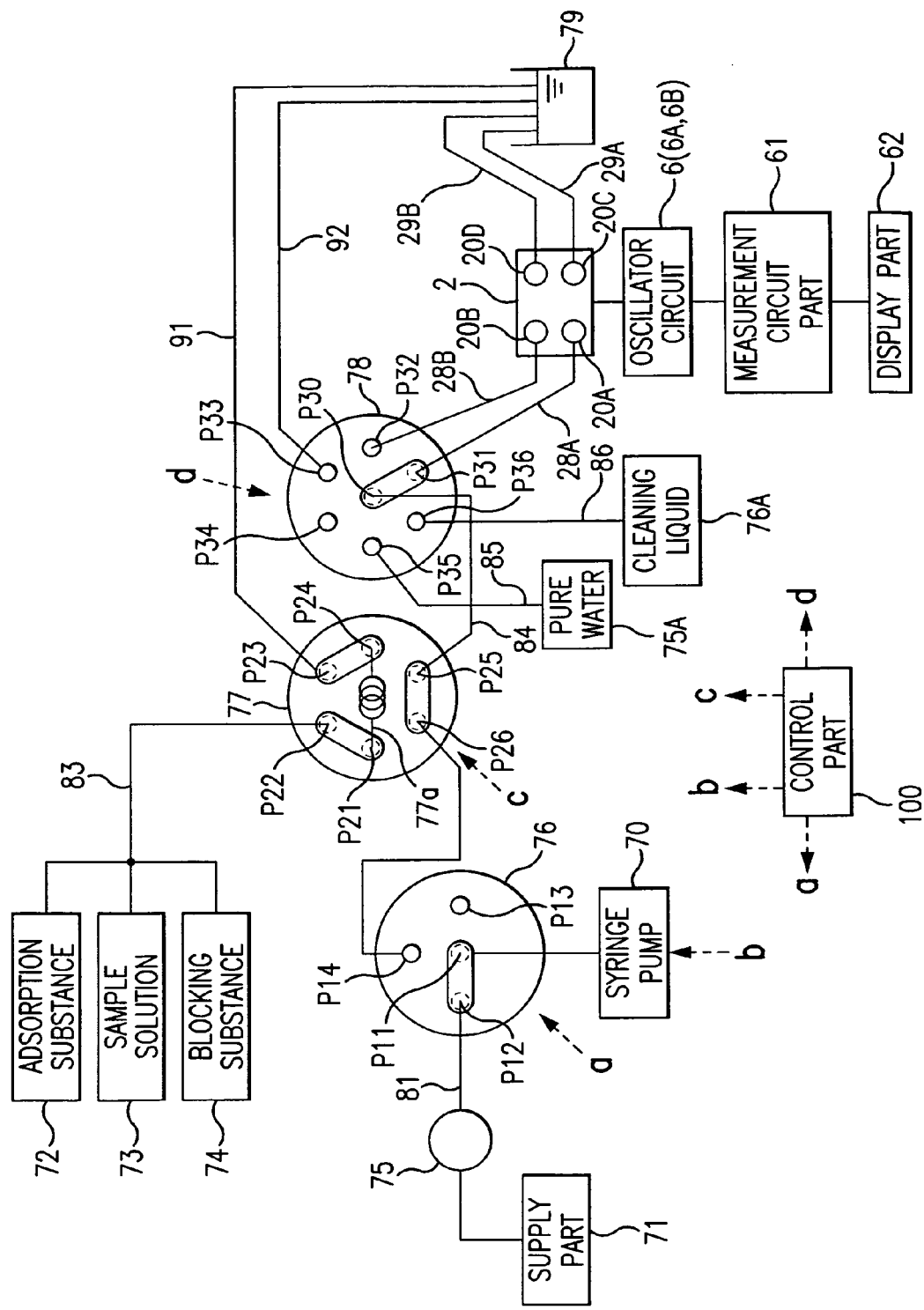
FIG. 8 is a block diagram schematically showing the whole structure of the sensing device.
Figure 11A:
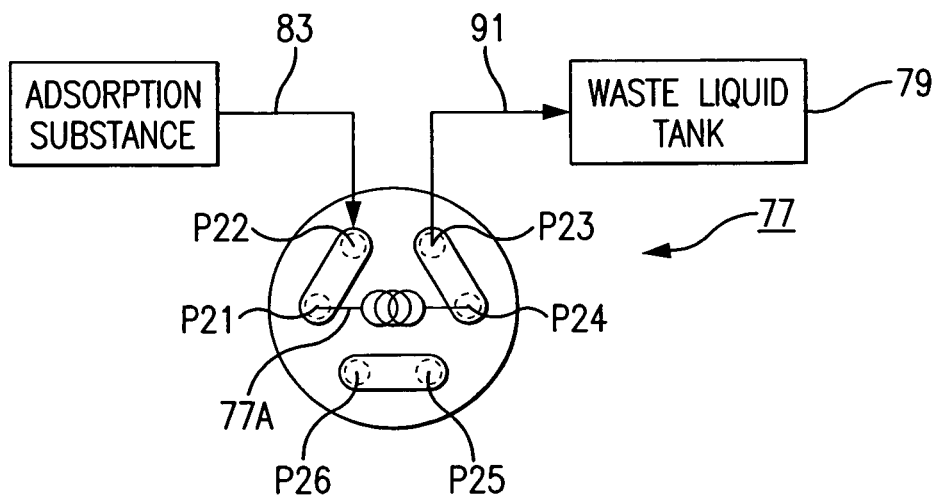
FIG. 11(a) and FIG. 11(b) are explanatory plane views showing switching control of a second valve provided in the sensing device.
Figure 11B:
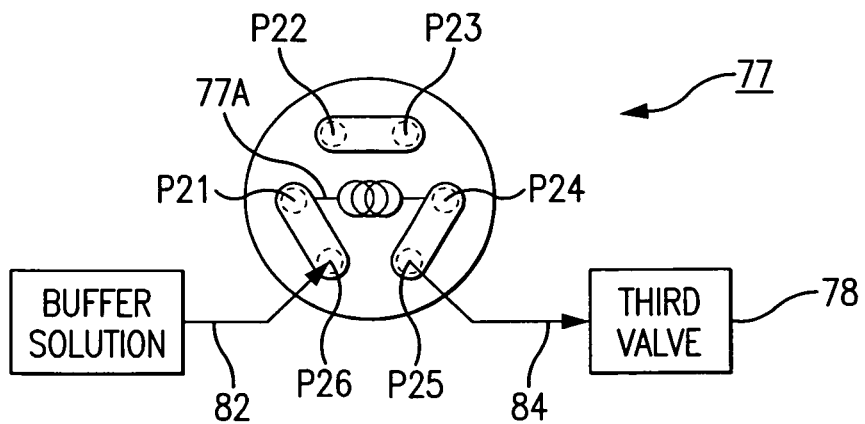

The second valve 77 includes, for example, injection valves, and as shown in, for example, FIG. 8, FIG. 11(*a*), and FIG. 11(*b*), it includes six ports P21 to P26 and an injection loop 77*a*. Among them, the port P26 is connected to the supply channel 82, and the port P22 is connected to the adsorption substance-containing solution supply part 72, the sample solution supply part 73, and the blocking substance-containing solution supply part 74 via a supply channel 83. The port P21 is connected to one end of the injection loop 77*a* and the port P24 is connected to the other end of the injection loop 77*a*. The port P25 is connected to the third valve 78 on a subsequent stage via a supply channel 84, and the port P23 is connected to the waste liquid tank 79 via a discharge channel 91.

As shown in FIG. 11(*a*), by switching the valves so as to connect the port P21 and the port P22, the port P23 and the port P24, and the port P25 and the port P26, the sample solution or the like is led into the injection loop 77*a* from the sample solution supply part 73 or the like via the supply channel 83 and the port P22. At this time, the sample solution or the like pushed out and flowing out from the inside of the injection loop 77*a* is sent to the waste liquid tank 79 via the discharge channel 91. Further, as shown in FIG. 11(*b*), the port P26, the port P21, the injection loop 77*a*, the port P24, and the port P25 are connected by switching the valves so as to connect the port P21 and the port P26, the port P22 and the port P23, and the port P24 and the port P25, so that the sample solution or the like led into the injection loop 77*a* is pushed out by the buffer solution led therein from the first valve 76 side via the supply channel 82 and the port P26 and is sent toward the third valve 78 via the supply channel 84.

Figure 12:
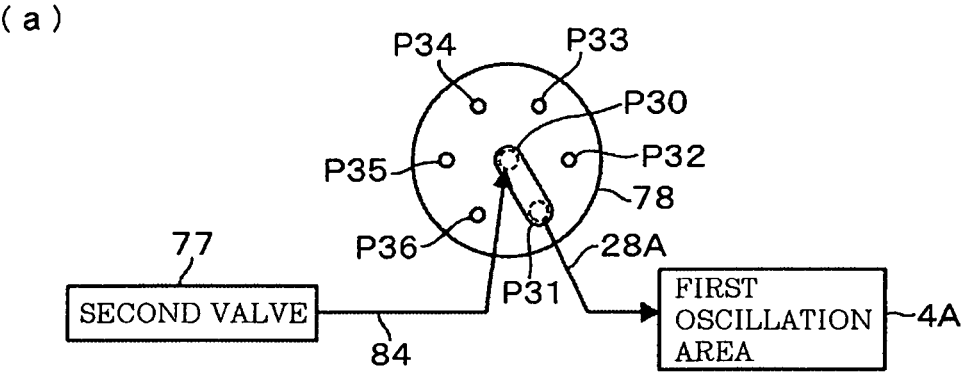
FIG. 12(a) to FIG. 12(c) are explanatory plane views showing switching control of a third valve provided in the sensing device.
Figure 12:
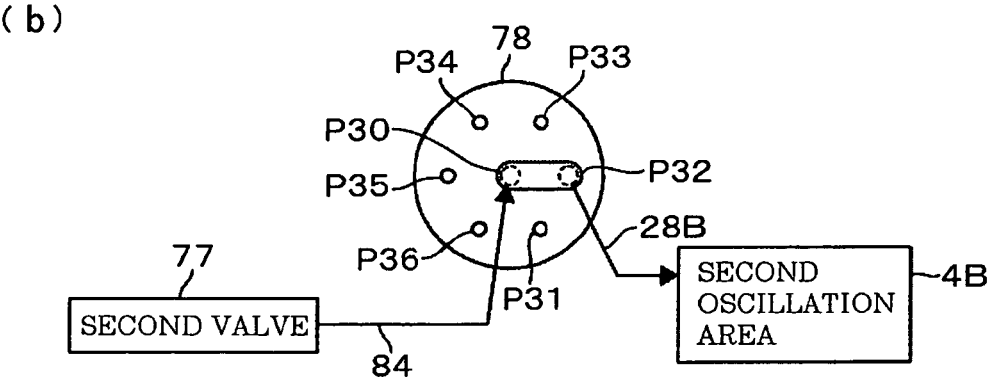
Figure 12:
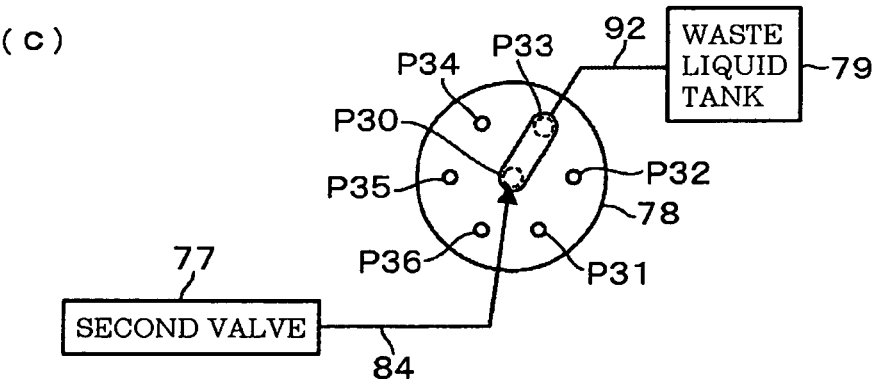

The third valve 78 includes, for example, a six-way valve, and for example, as shown in FIG. 8 and FIG. 12(*a*) to FIG. 12(*c*), includes ports P30 to P36. Among them, the port P30 is connected to the second valve 77 via the supply channel 84, the port P31 is connected to the liquid supply pipe 28A supplying a liquid to the first oscillation area 4A in the sensor unit 2, and the port P32 is connected to the liquid supply pipe 28B supplying a liquid to the second oscillation area 4B in the sensor unit 2. The port P33 is connected to the waste liquid tank 79 via a discharge channel 92, and the port P35 and the port P36 are connected to a pure water tank 75A and a cleaning liquid tank 76A via supply channels 85, 86, respectively. Further, the liquid discharge pipes 29A, 29B in the sensor unit 2 are connected to the waste liquid tank 79.

As shown in FIG. 12(*a*), by switching the valve so as to connect the port P30 and the port P31, the supply channel 84 extending from the second valve 77 and the liquid supply pipe 28A extending to the first oscillation area 4A are connected, so that the sample solution or the like is sent toward the first oscillation area 4A. As shown in FIG. 12(*b*), by switching the valve so as to connect the port P30 and the port P32, the supply channel 84 extending from the second valve 77 and the liquid supply pipe 28B extending to the second oscillation area 4B are connected, so that the sample solution or the like is sent to the second oscillation area 4B. As shown in FIG. 12(*c*), by switching the valve so as to connect the port P30 and the port P33, the supply channel 84 extending from the second valve 77 and the discharge channel 92 extending to the waste liquid tank 79 are connected, so that the sample solution or the like is sent toward the waste liquid tank 79.

In this example, a first supply channel connected to the first liquid storage space 53A is composed of the first supply channel 55A, the first liquid supply channel 26A, and the first liquid supply pipe 28A, and a second supply channel connected to the second liquid storage space 53B is composed of the second supply channel 55B, the second liquid supply channel 26B, and the second liquid supply pipe 28B. Further, a common channel for supplying the sample solution, the solution containing the adsorption substance, and the solution containing the blocking substance at different timings is composed of the supply channel 83, the second valve 77, and the supply channel 84, and a channel switcher switchably connecting the common channel to one of the first supply channel and the second supply channel is constituted by the third valve 78.

Figure 13:
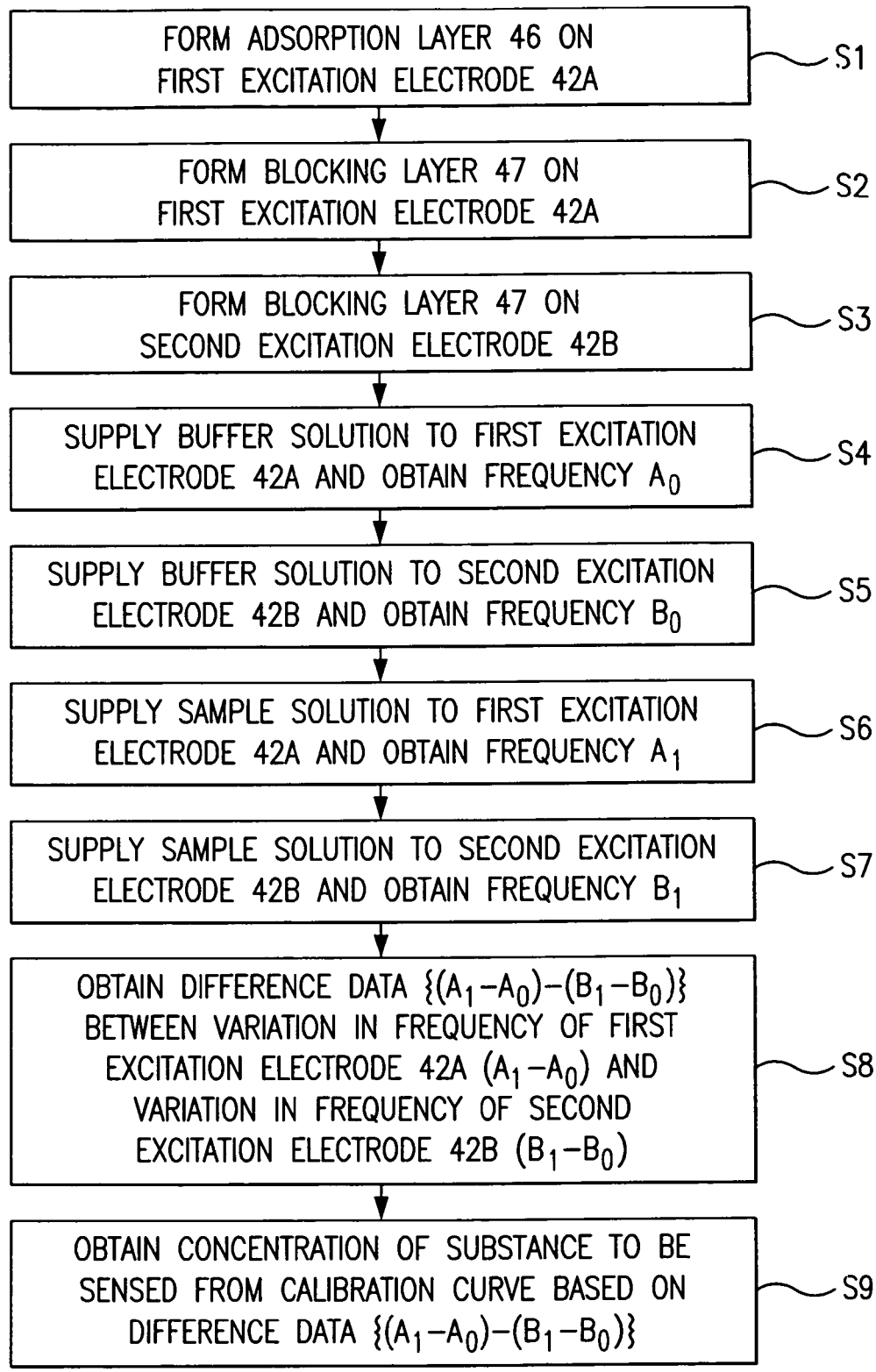
FIG. 13 is an explanatory flowchart showing the operation of the present invention.
Figure 14:
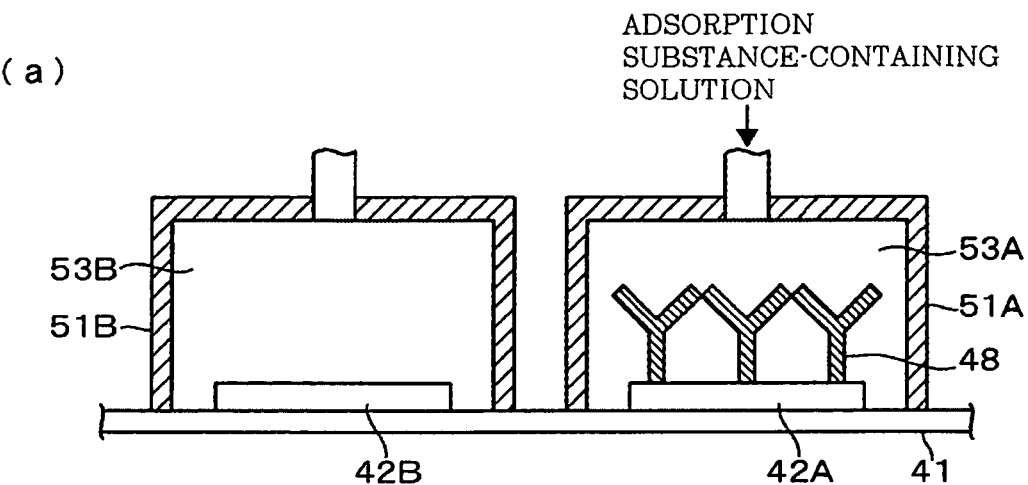
FIG. 14(a) to FIG. 14(c) are explanatory process views showing the operation of the present invention.
Figure 14:
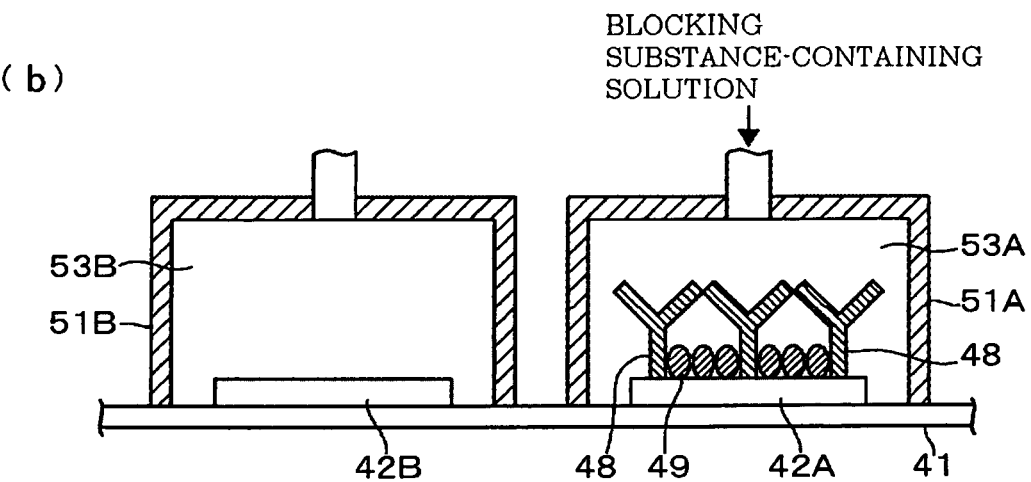
Figure 14:
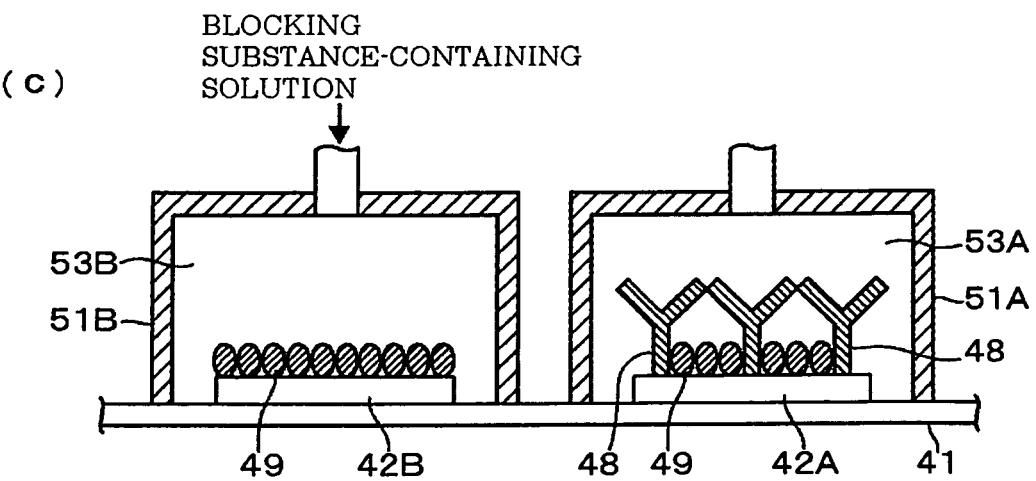

Next, the operation of the sensing device as structured above will be described by using FIG. 13 to FIG. 15(*a*) and FIG. 15(*b*). First, the quartz-crystal resonator 4 is mounted in the sensor unit 2 to be airtightly integrated with the sensor unit 2, and the oscillation areas 4A, 4B and the oscillator circuits 6A, 6B are electrically connected respectively via the connection terminals 35 to 37 formed on the wiring board 3. Then, prior to the measurement of the concentration of the substance to be sensed in the sample solution, a process of forming the adsorption layer 46 and the blocking layer 47 on the first excitation electrode 42A used as the reaction electrode and forming the blocking layer 47 on the second excitation electrode 42B used as the reference electrode is performed. This process will be described in detail. The adsorption layer 46 is formed on the front surface of the first excitation electrode 42A in such a manner that the adsorption substance-containing solution is led into the first liquid storage space 53A and the front surface of the first excitation electrode 42A is made to adsorb the adsorption substance 48 as shown in FIG. 14(*a*) (Step S1). Next, the blocking layer 47 is formed on the front surface of the first excitation electrode 42A in such a manner that the blocking substance-containing solution is led into the liquid storage space 53A and the blocking substance-containing solution is brought into contact with areas, of the front surface of the first excitation electrode 42A, on which the adsorption substance 48 is not adsorbed as shown in FIG. 14(*b*) (Step S2). Thereafter, the blocking layer 47 is formed on the front surface of the second excitation electrode 42B in such a manner that the blocking substance-containing solution is led into the second liquid storage space 53B and the front surface of the second excitation electrode 42B is made to adsorb the blocking substance 49 as shown in FIG. 14(*c*) (Step S3).

Subsequently, the oscillation of the quartz-crystal resonator 4 (oscillation areas 4A, 4B) is started with a predetermined frequency, for example, 30 MHz by the oscillator circuits 6A, 6B respectively, and at the same time, the sample solution is supplied to the first oscillation area 4A and the second oscillation area 4B, and the concentration of the substance to be sensed in the sample solution is detected. Specifically, as shown in FIG. 15(*a*), the butler solution is led into the first liquid storage space 53A, and a frequency AO when the oscillation frequency is stabilized is obtained (Step S4). Thereafter, the buffer solution is led into the second liquid storage space 53B, and a frequency BO when the oscillation frequency is stabilized is obtained (Step S5).

Figure 15A:
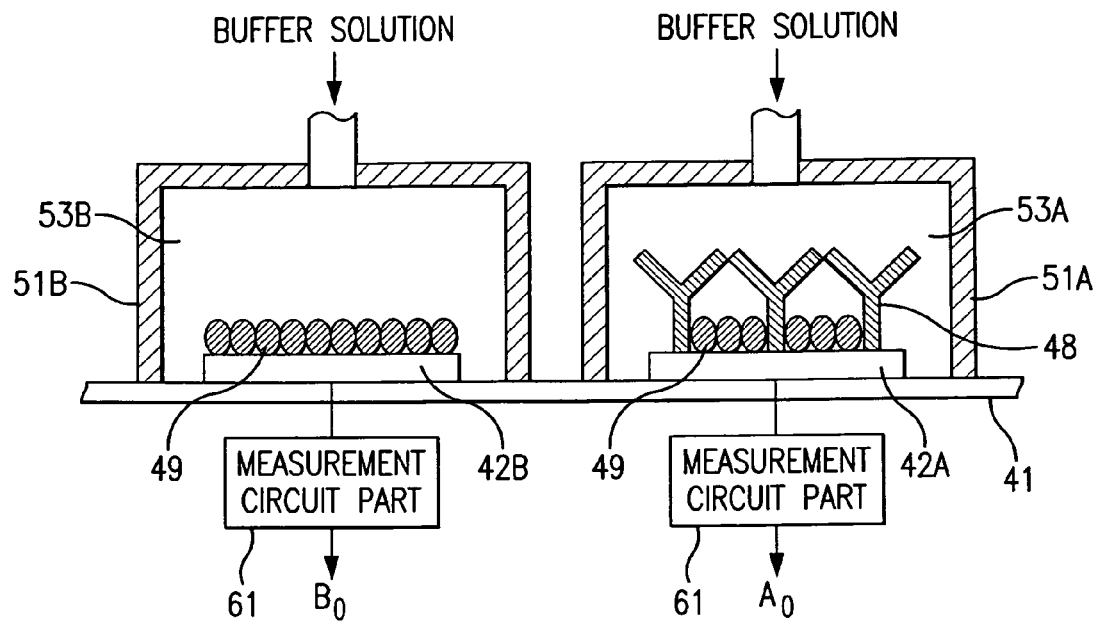
FIG. 15(a) and FIG. 15(b) are explanatory process views showing the operation of the present invention.
Figure 15B:
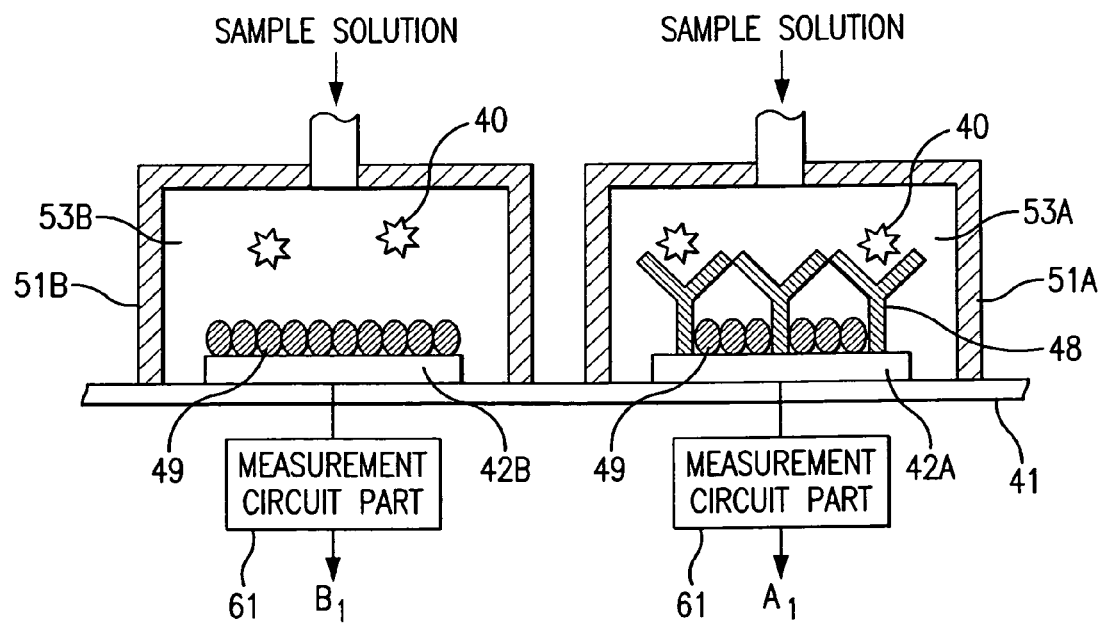

Subsequently, as shown in FIG. 15(*b*), the sample solution is led into the first liquid storage space 53A, and a frequency A1 when the oscillation frequency is stabilized is obtained (Step S6). When the solution containing the substance to be sensed is thus supplied, the substance to be sensed (antigen) 40 is selectively captured by the adsorption substance (antibody) due to the antigen-antibody reaction, and the resonance frequency (natural frequency) of the first oscillation area 4A changes according to an adsorption amount of the substance to be sensed. Next, the sample solution is led into the second liquid storage space 53B, and a frequency B1 when the oscillation frequency is stabilized is obtained (Step S7).

Then, difference data $\{(A1-A0)-(B1-B0)\}$ between a variation (A1-A0) in the frequency of the first excitation electrode 42A and a variation (B1-B0) in the frequency of the second excitation electrode 42B is calculated (Step S8), and the concentration of the substance to be sensed is obtained according to the difference data $\{(A1-A0)-(B1-B0)\}$ based on a relation expression (calibration curve) found beforehand (Step S9). At this time, the aforesaid frequency acquisition, the storage of the obtained data, and the determination of the concentration of the substance to be sensed in Step S4 to Step S9 are performed in the measurement circuit part 61, and the measurement result is displayed on the display part 62, for instance. Thereafter, the quartz-crystal resonator 4 used for the measurement is detached from the sensor unit 2, and a new quartz-crystal resonator 4 is mounted in the sensor unit 2, followed by the next measurement.

At this time, for forming the adsorption layer 46 on the front surface of the first excitation electrode 42A, a predetermined amount of the adsorption substance-containing solution is first led into the injection loop 77*a* by switching the second valve 77 to the position shown in FIG. 11(*a*). Next, the second valve 77 is switched to the position shown in FIG. 11(*b*). At the same time, by switching the first valve 76 to the position shown in FIG. 10(*a*) a predetermined amount of the buffer solution is led into the first valve 76, and next, by switching the valve 76 to the position shown in FIG. 10(*b*) a predetermined amount of the buffer solution is led into the injection loop 77*a*. As a result, the adsorption substance-containing solution in the injection loop 77*a* is pushed out by the buffer solution to be sent toward the third valve 78 from the second valve 77. In the third valve 78, by switching the valve to the position shown in FIG. 12(*a*), the adsorption substance-containing solution is selectively supplied into the first liquid storage space 53A, so that the adsorption layer 46 containing the adsorption substance is formed on the front surface of the first excitation electrode 42A.

Subsequently, for forming the blocking layer 47 on the front surface of the first excitation electrode 42A, a predetermined amount of the blocking substance-containing solution is led into the injection loop 77*a* from the blocking substance-containing solution supply part 74, by switching the second valve 77 to the position shown in FIG. 11(*a*), and accordingly the buffer solution remaining in the injection loop 77*a* is pushed out by the blocking substance-containing solution to be discharged to the waste liquid tank 79 via the discharge channel 91. Next, by switching the second valve 77 to the position shown in FIG. 10(*b*), a predetermined amount of the buffer solution is led into the injection loop 77*a* as previously described, and accordingly, the blocking substance-containing solution in the injection loop 77*a* is pushed out by the buffer solution to be sent toward the third valve 78. In the third valve 78, by switching the valve to the position shown in FIG. 12(*a*), the blocking substance-containing solution is selectively supplied into the first liquid storage space 53A, so that the blocking layer 47 is formed on the front surface of the first excitation electrode 42A.

Next, for forming the blocking layer 47 on the front surface of the second excitation electrode 42B, the blocking substance-containing solution sent toward the third valve 78 is selectively supplied into the second liquid storage space 53B by switching the third valve 78 to the position shown in FIG. 12(*b*), so that the blocking layer 47 is formed on the front surface of the second excitation electrode 42B.

Thereafter, the buffer solution is supplied to the first excitation electrode 42A and the second excitation electrode 43B, and at this time, by keeping the second valve 77 switched to the position shown in FIG. 11(*b*), the buffer solution is kept supplied to the injection loop 77*a* of the second valve 77 via the first valve 76. Consequently, the buffer solution is sent toward the third valve 78. By switching the third valve 78 to the position shown in FIG. 12(*a*), a predetermined amount of the buffer solution is first supplied to the first liquid storage space 53A. Thereafter, by switching the valve 78 to the position shown in FIG. 12(*b*), a predetermined amount of the buffer solution is supplied into the second liquid storage space 53B.

Subsequently, the sample solution is supplied to the first excitation electrode 42A and the second excitation electrode 43B, and at this time, by switching the second valve 77 to the position shown in FIG. 11(*a*) as previously described, a predetermined amount of the sample solution is led into the injection loop 77*a*. At this time, the buffer solution remaining in the injection loop 77*a* is discharged to the waste liquid tank 79. Next, the second valve 77 is switched to the position shown in FIG. 11(*b*) and the first valve 76 is switched, so that a predetermined amount of the buffer solution is led into the injection loop 77*a*, and consequently the sample solution in the injection loop 77*a* is pushed out by the buffer solution to be sent toward the third valve 78. In the third valve 78, the valve is first switched to the position for supplying the sample solution to the first liquid storage space 53A, whereby a predetermined amount of the sample solution in the injection loop 77*a*, for example, a half amount thereof is supplied to the liquid storage space 53A. Thereafter, the valve 78 is switched to the position for supplying the sample solution to the second liquid storage space 53B, whereby a predetermined amount of the sample solution in the injection loop 77*a*, for example, a residual amount thereof is supplied to the liquid storage space 53B.

In the above-described embodiment, since the first oscillation area 4A and the second oscillation area 4B are formed on the common quartz-crystal piece 41, the oscillation areas 4A, 4B have the same frequency characteristic. Therefore, by using the first excitation electrode 4A as the reaction electrode and using the second excitation electrode 42B as the reference electrode, and taking a difference between the oscillation frequencies of the oscillation areas 4A, 4B, it is possible to cancel a frequency variation accompanying external disturbances such as the adhesion of a substance other than the substance to be sensed in the sample solution and the viscosity of the sample solution because frequency variations due to these external disturbances are equal both for the oscillation frequencies A1, B1 of the oscillation areas 4A, 4B when the both areas are brought into contact with the sample solution. Therefore, when the difference between the oscillation frequencies A1, B1 of the oscillation areas 4A, 4B when these areas are brought into contact with the sample solution (A1-B1) and the difference between the oscillation frequencies A0, B0 of the oscillation areas 4A, 4B when these areas are brought into contact with the buffer solution (A0-B0) are compared, the obtained variation {(A1-B1)–(A0-B0)} between these differences can be regarded as a frequency variation ascribable to an amount of the substance to be sensed in the sample solution. Consequently, it is possible to obtain a highly reliable variation in the oscillation frequency.

Further, in this sensing device, by using the pressing member 5, the liquid storage spaces 53A, 53B separated from each other are formed on the front surface of the first excitation electrode 42A and on the front surface of the second excitation electrode 42B. This makes it possible to supply liquid such as the sample solution individually to the liquid storage spaces 53A, 53B. Therefore, it is possible to form the adsorption layer 46 and the blocking layer 47 on the first excitation electrode 42A and form only the blocking layer 47 on the second excitation electrode 42B after the quartz-crystal resonator 4 is mounted in the sensing device, by a simple method of supplying the adsorption substance-containing solution and the blocking substance-containing solution to the first liquid storage space 53A and supplying the blocking substance-containing solution to the second liquid storage space 53B. This eliminates a need for a troublesome pre-process of forming the blocking layer 47 on one of the quartz-crystal resonators 4 before the quartz-crystal resonator 4 is mounted in the sensing device, which reduces the trouble and shortens the time required for the pre-process, resulting in the prevention of an increase in the total measurement time.

In the above-described example, the buffer solution functions as the pushing liquid for pushing the blocking substance-containing solution and the sample solution in the injection loop 77a and further functions as the reference liquid not containing the substance to be sensed, which is supplied to the first excitation electrode 42A and the second excitation electrode 43B. However, the pushing liquid and the reference liquid are not limited to the buffer solution and may be pure water or the like, for instance. Since the buffer solution is an example of the reference liquid, the buffer solution reservoir part 71 is a reference liquid supply source.

Figure 16:
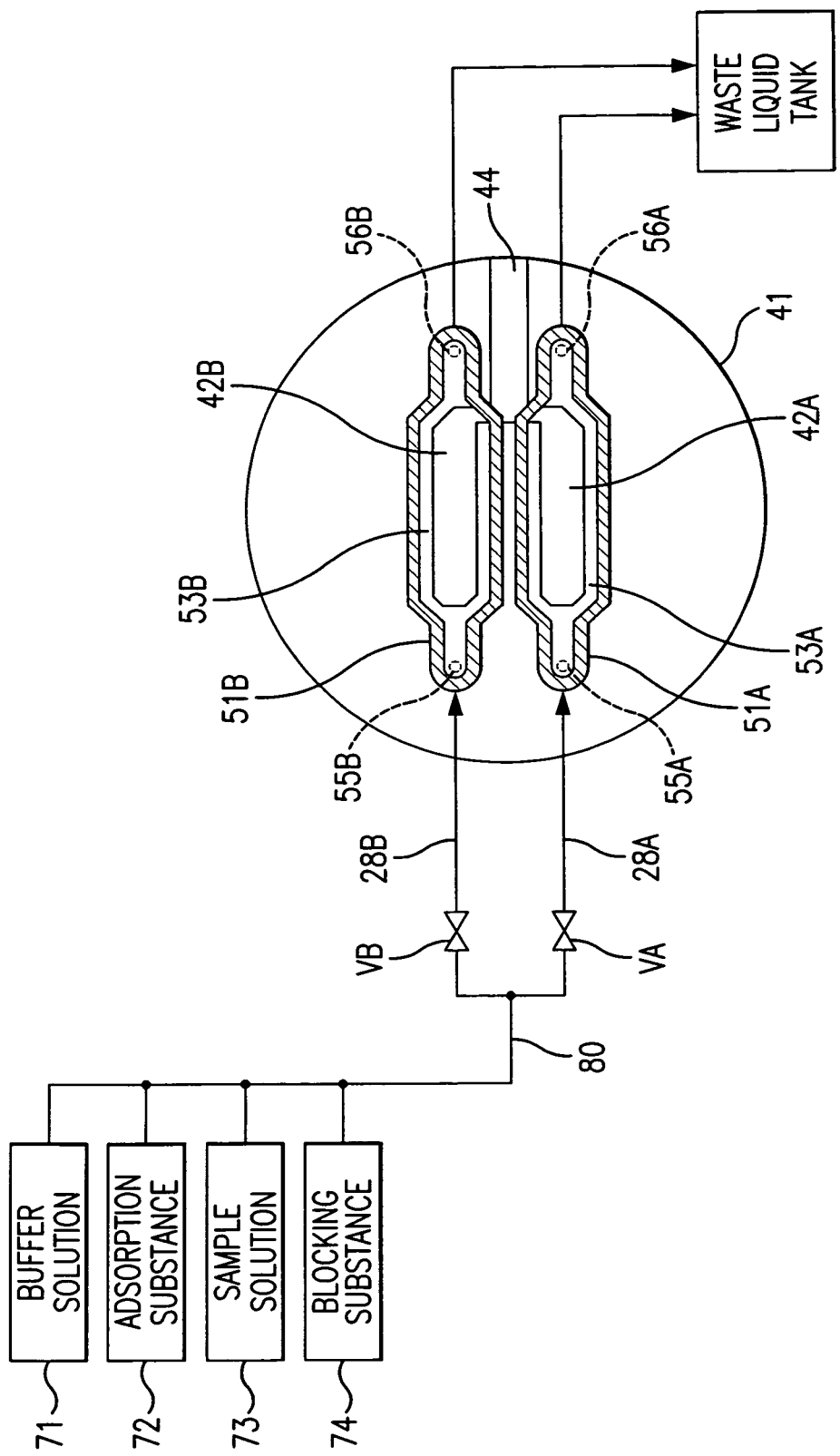
FIG. 16 is a plane view showing another embodiment of the present invention.

A system for supplying the adsorption substance-containing solution, the sample solution, and so on to the sensor unit 2 may be structured as shown in FIG. 16. In this example, as a channel switcher switchably supplying the liquid to one of the liquid supply channels 28A, 28B for supplying the liquid to the liquid storage spaces 53A, 53B in the sensor unit 2, opening/closing valves VA, VB are provided and the buffer solution reservoir part 71, the adsorption substance-containing solution supply part 72, the sample solution supply part 73, and the blocking substance-containing solution supply part 74 are connected to upstream sides of the opening/closing valves VA, VB via a common channel 80. By switching the opening/closing valves VA, VB, the liquid is supplied switchably to one of the two liquid storage spaces 53A, 53B.

This structure enables the liquid supply to one of the two liquid storage spaces 53A, 53B or enables the simultaneous liquid supply to both of the liquid storage spaces 53A, 53B. Therefore, the liquid supply may take place as follows, for example. Only the valve VA is opened to supply the adsorption substance-containing solution selectively to the first liquid storage space 53A so that the first excitation electrode 42A adsorbs the adsorption substance, thereafter, the valves VA, VB are both opened to supply the blocking substance-containing solution simultaneously to the first liquid storage space 53A and the second liquid storage space 53B so that the area, in the first excitation electrode 42A, on which the adsorption substance is not formed, and the front surface of the second excitation electrode 42B adsorb the blocking substance, and next, the first liquid storage space 53A and the second liquid storage space 53B are simultaneously supplied with the buffer solution and the sample solution in this order.

In this case, for obtaining the oscillation frequencies when the first and second liquid storage spaces 53A, 53B are simultaneously supplied with the buffer solution and the sample solution, the frequency signals from the first and second oscillator circuits 6A, 6B may be alternately fetched in a time-division manner by alternate switching of the switch part 63 at 1 ms time interval, for instance. Then, the measurement circuit part 61 may decide an amount (concentration) of the substance to be sensed by calculating the difference data (A1-A0) and the difference data (B1-B0) of the oscillation frequencies A0, A1 and the oscillation frequencies B0, B1 obtained from the first oscillation area 4A and the second oscillation area 4B, respectively, in the same time zone, calculating the difference data {(A1-A0)–(B1-B0)}, obtaining time-series data of the difference data to store the obtained difference data in the memory, and reading the concentration corresponding to the difference data {(A1-A0)–(B1-B0)} based on the calibration curve obtained in advance.

Here, the simultaneous liquid supply to the first and second liquid storage spaces 53A, 53B includes not only a case where the liquid is supplied at the same timing but also a case where, during the liquid supply to one of the liquid storage spaces, the liquid supply to the other liquid storage space is started.

In the foregoing, the liquid storage spaces 53A, 53B formed in the first oscillation area 4A and the second oscillation area 4B respectively may be formed as follows. At positions, in the pressing member 5, corresponding to the first excitation electrode 42A and the second excitation electrode 42B, hole portions larger than the excitation electrodes 42A, 42B are formed and the hole portions are covered by the supply/discharge cover 24, whereby the liquid storage space 53A, 53B being closed spaces are formed around the first excitation electrode 42A and the second excitation electrode 42B respectively by the pressing member 5 and the supply/discharge cover 24.

Further, the first space forming member and the second space forming member may be provided separately from the pressing member 5 pressing the quartz-crystal piece 41 against the wiring board 3. In this case, for example, the first and second space forming members are formed so as to surround front surface sides, lateral sides, and upper sides of the excitation electrode 42A and the excitation electrode 42B respectively, and the pressing member 5 and the supply/discharge cover 24 are provided from above the first and second space forming members. In this case, the first and second space forming members may be independently provided or may be integrally provided. Further, the first and second space forming members each may be entirely made of an elastic member or it suffices that only at least their portions in contact with the quartz-crystal resonator are made of the elastic member.

Further, in the present invention, the difference data of the oscillation frequencies of the first oscillation area and the second oscillation area may be used, for example, for creating the calibration curve showing a correspondence relation between the concentration of the substance to be sensed in the sample solution and a decrease amount of the frequency or maybe used for detecting the presence/absence of the substance to be sensed in the sample solution. Further, the present invention is applicable to the sensing of a C-reactive protein (CRP) being a substance to be sensed in a serum being a sample solution.

What is claimed is:

1. A sensing device in which a piezoelectric resonator having a first oscillation area and a second oscillation area formed on a common piezoelectric piece and oscillating independently of each other is mounted and which senses a substance to be sensed in a sample solution based on variations in oscillation frequencies of both oscillation areas when the sample solution is brought into contact with one surface side of the piezoelectric resonator, the sensing device comprising:
   a first space forming member forming a first liquid storage space for supplying liquid to one surface side of the first oscillation area;
   a second space forming member forming a second liquid storage space for supplying liquid to one surface side of the second oscillation area, the second liquid storage space being separated from the first liquid storage space;
   a supply channel supplying a solution containing an adsorption substance that adsorbs the substance to be sensed in the sample solution selectively to the first liquid storage space to make an electrode in the first oscillation area adsorb the adsorption substance;
   a supply channel supplying a solution containing a blocking substance that prevents the adsorption of the substance to be sensed and a substance other than the substance to be sensed within the sample solution, to the first liquid storage space and the second liquid storage space in order to make the electrode in the first oscillation area and an electrode in the second oscillation area adsorb the blocking substance;
   a supply channel supplying the sample solution to the first liquid storage space and the second liquid storage space; and
   a liquid discharge channel for liquid discharge from the first liquid storage space and the second liquid storage space.

2. The sensing device according to claim 1, further comprising:
   a first supply channel and a second supply channel connected to the first liquid storage space and the second liquid storage space, respectively;
   a common channel connected to upstream sides of the first supply channel and the second supply channel and supplying the sample solution, the solution containing the adsorption substance, and the solution containing the blocking substance at different timings; and
   a channel switcher switchably connecting the common channel to one of the first supply channel and the second supply channel.

3. The sensing device according to claim 2, further comprising:
   a reference liquid supply source provided on an upstream side of the common channel to supply a reference liquid not containing the substance to be sensed; and
   a controller controlling the channel switcher to cause the supply of the solution containing the adsorption substance, the solution containing the blocking substance, the reference liquid, and the sample solution in the order cited to the first supply channel and the supply of the solution containing the blocking substance, the reference liquid, and the sample solution in the order cited to the second supply channel.

4. The sensing device according to claim 1, wherein the adsorption substance is an antibody and the substance to be sensed in the sample solution is an antigen.

5. The sensing device according to claim 1, wherein in the first space forming member and the second space forming member, at least portions in contact with the piezoelectric resonator are each made of an elastic member.

6. A sensing method in which a piezoelectric resonator having a first oscillation area and a second oscillation area formed on a common piezoelectric piece and oscillating independently of each other is mounted and a substance to be sensed in a sample solution is sensed based on variations in oscillation frequencies of both oscillation areas when the sample solution is brought into contact with one surface side of the piezoelectric resonator, the sensing method comprising:
   providing a first space forming member forming a first liquid storage space for supplying liquid to one surface side of the first oscillation area and a second space forming member forming a second liquid storage space for supplying liquid to one surface side of the second oscillation area, the second liquid storage space being separated from the first liquid storage space;
   supplying a solution containing an adsorption substance that adsorbs the substance to be sensed in the sample solution to the first liquid storage space to make an electrode in the first oscillation area adsorb the adsorption substance;
   next supplying a solution containing a blocking substance that prevents the adsorption of the substance to be sensed and a substance other than the substance to be sensed within the sample solution, to the first liquid storage space to make the electrode in the first oscillation area adsorb the blocking substance;
   supplying the solution containing the blocking substance to the second liquid storage space to make an electrode in the second oscillation area adsorb the blocking substance;
   supplying a reference liquid not containing the substance to be sensed and the sample solution in the order cited to the first liquid storage space to measure the oscillation frequency of the first oscillation area; and
   supplying the reference liquid not containing the substance to be sensed and the sample solution in the order cited to the second liquid storage space to measure the oscillation frequency of the second oscillation area.

* * * * *